(12) United States Patent
Koh et al.

(10) Patent No.: US 10,786,811 B1
(45) Date of Patent: Sep. 29, 2020

(54) DETECTION OF ACTIVE AND LATENT INFECTIONS WITH MICROFLUIDIC DEVICES AND SYSTEMS THEREOF

(71) Applicants: National Technology & Engineering Solutions of Sandia, LLC, Albuquerque, NM (US); Julia Litvinov, Galveston, TX (US)

(72) Inventors: Chung-Yan Koh, Dublin, CA (US); Anup K. Singh, Danville, CA (US); Julia Litvinov, Galveston, TX (US)

(73) Assignees: National Technology & Engineering Solutions of Sandia, LLC, Albuquerque, NM (US); Julia Litvinov, Galveston, TX (US)

( * ) Notice: Subject to any disclaimer, the term of this patent is extended or adjusted under 35 U.S.C. 154(b) by 261 days.

(21) Appl. No.: 15/785,708

(22) Filed: Oct. 17, 2017

Related U.S. Application Data

(60) Provisional application No. 62/412,153, filed on Oct. 24, 2016.

(51) Int. Cl.
| | | |
|---|---|---|
| G01N 33/00 | (2006.01) | |
| B01L 3/00 | (2006.01) | |
| G01N 33/53 | (2006.01) | |
| G01N 35/00 | (2006.01) | |
| B01J 4/02 | (2006.01) | |
| G01N 35/08 | (2006.01) | |

(52) U.S. Cl.
CPC ............ B01L 3/502715 (2013.01); B01J 4/02 (2013.01); G01N 33/5302 (2013.01); G01N 35/00069 (2013.01); G01N 35/08 (2013.01); B01L 2200/027 (2013.01); B01L 2300/0864 (2013.01)

(58) Field of Classification Search
CPC ................................................. B01L 3/502715
USPC .......................................... 436/149; 422/502
See application file for complete search history.

(56) References Cited

U.S. PATENT DOCUMENTS

| | | |
|---|---|---|
| 3,555,284 A | 1/1971 | Anderson |
| 3,744,974 A | 7/1973 | Maddox |
| 4,125,375 A | 11/1978 | Hunter |
| 4,156,570 A | 5/1979 | Wardlaw |
| 4,554,071 A | 11/1985 | Ruijten et al. |
| 4,656,143 A | 4/1987 | Baker et al. |
| 4,683,579 A | 7/1987 | Wardlaw |
| 4,844,818 A | 7/1989 | Smith |
| 5,279,936 A | 1/1994 | Vorpahl |

(Continued)

FOREIGN PATENT DOCUMENTS

| | | |
|---|---|---|
| WO | WO 2008/143578 | 11/2008 |
| WO | WO 2009/098237 | 8/2009 |

OTHER PUBLICATIONS

U.S. Appl. No. 13/423,008, filed Mar. 16, 2012, Koh et al.

(Continued)

*Primary Examiner* — Christopher Adam Hixson
*Assistant Examiner* — Emily R. Berkeley
(74) *Attorney, Agent, or Firm* — Helen S. Baca

(57) ABSTRACT

The present invention relates to methods of detecting one or more targets of interest in a sample. In one instance, the target can be correlated to an active infection (e.g., by a virus and/or a bacterium). Methods can include treating the sample with a dissociation agent, thereby releasing the target of interest for more accurate detection (e.g., by use of a sedimentation-based centrifugal microfluidic devices). Also described herein are microfluidic devices and systems for use with a dissociation agent.

19 Claims, 12 Drawing Sheets

(56) References Cited

U.S. PATENT DOCUMENTS

| | | | |
|---|---|---|---|
| 5,635,362 | A | 6/1997 | Levine et al. |
| 5,639,428 | A | 6/1997 | Cottingham |
| 5,705,628 | A | 1/1998 | Hawkins |
| 5,882,903 | A | 3/1999 | Andrevski et al. |
| 5,892,577 | A | 4/1999 | Gordon |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 6,960,449 | B2 | 11/2005 | Wang et al. |
| 7,033,747 | B2 | 4/2006 | Gordon et al. |
| 7,157,049 | B2 | 1/2007 | Valencia et al. |
| 7,312,085 | B2 | 12/2007 | Chou et al. |
| 7,332,326 | B1 | 2/2008 | Kellogg et al. |
| 7,758,810 | B2 | 7/2010 | Lee et al. |
| 8,337,775 | B2 | 12/2012 | Pugia et al. |
| 8,945,914 | B1 | 2/2015 | Schaff et al. |
| 8,962,346 | B2 | 2/2015 | Schaff et al. |
| 9,186,668 | B1 | 11/2015 | Schaff et al. |
| 9,244,065 | B1 | 1/2016 | Schaff et al. |
| 9,304,128 | B1 | 4/2016 | Koh et al. |
| 9,304,129 | B2 | 4/2016 | Schaff et al. |
| 9,500,579 | B1 | 11/2016 | Sommer et al. |
| 9,702,871 | B1 | 7/2017 | Koh et al. |
| 2001/0055812 | A1 | 12/2001 | Mian et al. |
| 2002/0098535 | A1 | 7/2002 | Wang et al. |
| 2002/0106786 | A1 | 8/2002 | Carvalho et al. |
| 2002/0137068 | A1 | 9/2002 | Haugland et al. |
| 2002/0151043 | A1 | 10/2002 | Gordon |
| 2002/0153251 | A1 | 10/2002 | Sassi et al. |
| 2002/0164659 | A1 | 11/2002 | Rao et al. |
| 2002/0170825 | A1 | 11/2002 | Lee et al. |
| 2003/0013203 | A1 | 1/2003 | Jedrzejewski et al. |
| 2003/0124719 | A1 | 7/2003 | Woodside |
| 2003/0203504 | A1 | 10/2003 | Hefti |
| 2004/0072278 | A1 | 4/2004 | Chou et al. |
| 2005/0186685 | A1 | 8/2005 | Kange et al. |
| 2005/0215410 | A1 | 9/2005 | Merino et al. |
| 2005/0282220 | A1 | 12/2005 | Prober et al. |
| 2006/0171654 | A1 | 8/2006 | Hawkins et al. |
| 2008/0108047 | A1 | 5/2008 | Woodside |
| 2008/0149484 | A1 | 6/2008 | Tolley et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2011/0045958 | A1 | 2/2011 | Pedrazzini |
| 2013/0260447 | A1 | 10/2013 | Link |
| 2014/0273241 | A1 | 9/2014 | Ochranek et al. |
| 2015/0360225 | A1 | 12/2015 | Schaff et al. |
| 2016/0061829 | A1 | 3/2016 | Schaff et al. |
| 2016/0178619 | A1 | 6/2016 | Koh et al. |

OTHER PUBLICATIONS

U.S. Appl. No. 13/941,186, filed Jul. 12, 2013, Koh et al.
U.S. Appl. No. 14/090,040, filed Nov. 26, 2013, Koh et al.
U.S. Appl. No. 14/957,405, filed Dec. 2, 2015, Koh.
U.S. Appl. No. 15/616,740, filed Jun. 7, 2017, Koh et al.
U.S. Appl. No. 15/669,426, filed Aug. 4, 2017, Phaneuf et al.
U.S. Appl. No. 15/704,860, filed Sep. 14, 2017, Koh et al.
Aaron et al., "Tuberculosis in HIV-infected patients: a comprehensive review", Clinical Microbiology and Infection, 2004, vol. 10(5), pp. 388-398.
Abi-Samra et al., "Infrared controlled waxes for liquid handling and storage on a CD-microfluidic platform", Lab on a Chip, 2011, vol. 11, pp. 723-726.
Ahanotu et al., "Staphylococcal enterotoxin B as a biological weapon: recognition, management, and surveillance of Staphylococcal enterotoxin", Applied Biosafety, 2006, vol. 11 (3), pp. 120-126.
Ahmed et al., "HIV-1/Mycobacterium tuberculosis coinfection immunology: How does HIV-1 exacerbate tuberculosis", Infection and Immunology, 2011, vol. 79, pp. 1407-1417.
Albrecht et al., "Micro free-flow IEF enhanced active cooling and functionalized gels", Electrophoresis, 2006, vol. 27, pp. 4960-4969.
Amersham Biosciences AB, "Percoll: methodology and applications", Handbook No. 18-1115-69 (Ed. AC), 2001, Uppsala, Sweden, pp. 1-84.
Amoakwa et al., "Risk factors for developing active tuberculosis after the treatment of latent tuberculosis in adults infected with human immunodeficiency virus", Open Forum Infectious Diseases, 2015, vol. 2(1), Article ofu120 (4 pp.).
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytical Chemistry, 2007, vol. 79(11), pp. 4022-4030.
Armitige et al., "Disruption of the genes encoding antigen 85A and antigen 85B of Mycobacterium tuberculosis H37Rv: effect on growth in culture and in macrophages", Infection and Immunity, 2000, vol. 68(2), pp. 767-778.
Baba et al., "Evaluation of immune responses in HIV infected patients with pleural tuberculosis by the QuantiFERON® TB-Gold interferon-gamma assay", BMC Infectious Diseases, 2008, vol. 8, Article 35 (8 pp.).
Baldwin, "How Hofmeister ion interactions affect protein stability", Biophysical Journal, 1996, vol. 71, pp. 2056-2063.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Bernard et al., "Laboratory testing for the diagnosis of HIV infection: updated recommendations", Centers for Disease Control and Prevention, 2014, (68 pp.), available at stacks.cdc.gov/view/cdc/23447.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Cabrera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings,1990, vol. 27, pp. 99-100.
Churchill et al., "Detection of Listeria monocytogenes and the toxin listeriolysin O in food", Journal of Microbiological Methods, 2006, vol. 64(2), pp. 141-170.
Corstjens et al., "Rapid assay format for multiplex detection of humoral immune responses to infectious disease pathogens (HIV, HCV, and TB)", Annals of the New York Academy of Sciences, 2007, vol. 1098, pp. 437-445.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.
Czeiger et al., "Measurement of circulating cell-free DNA levels by a new simple fluorescent test in patients with primary colorectal cancer", American Journal of Clinical Pathology, 2011, vol. 135(2), pp. 264-270.
Daniel et al., "The serodiagnosis of tuberculosis and other mycobacterial diseases by enzyme-linked immunosorbent assay", American Review of Respiratory Disease, 1987, vol. 135(5), pp. 1137-1151.
Das et al., "Effects of separation length and voltage on isoelectric focusing in a plastic microfluidic device", Electrophoresis, 2006, vol. 27(18), pp. 3619-3626.

(56) References Cited

OTHER PUBLICATIONS

Dheda et al., "Point-of-care diagnostics of tuberculosis: past, present and future", Respirology, 2013, vol. 18, pp. 217-232.
Dierberg et al., "Human immunodeficiency virus-associated tuberculosis: Update on prevention and treatment", Clinics in Chest Medicine, 2013, vol. 34, pp. 217-228.
Du Toit et al., "Tuberculosis chemotherapy: current drug delivery approaches", Respiratory Research, 2006, vol. 7, Article 118 (18 pp.).
Elhassan et al., "The impact of mass gathering on the burden of multidrug resistant Mycobacterium tuberculosis in Al-Madinah Al-Monawarah region, Saudi Arabia", Infectious Disorders—Drug Targets, Nov. 2016, PubMed: 27848902 (Abstract, 1 p.).
Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.
Espitia et al., "A 38-kD Mycobacterium tuberculosis antigen associated with infection: its isolation and serologic evaluation", Clinical & Experimental Immunology, 1989, vol. 77, pp. 373-377.
Fologea et al, "Detecting single stranded DNA with a solid state nanopore", Nano Letters, 2005, vol. 5(10), pp. 1905-1909.
Getahun et al., "HIV infection-associated tuberculosis: the epidemiology and the response", Clinical Infectious Diseases, 2010, vol. 50 (Supp. 3), pp. S201-S207.
Glorikian et al., "Microfluidics for IVDS—Smart consumable product development: implications for molecular diagnostics", DX Directions 2010, Spring, pp. 12-16.
Goldshtein et al., "A rapid direct fluorescent assay for cell-free DNA quantification in biological fluids", Annals of Clinical Biochemistry, 2009, vol. 46(Pt 6), pp. 488-494.
Görg et al., "Recent developments in two-dimensional gel electrophoresis with immobilized pH gradients: wide pH gradients up to pH 12, longer separation distances and simplified procedures", Electrophoresis, 1999, vol. 20(4-5), pp. 712-717.
Görg et al., "The current state of two-dimensional electrophoresis with immobilized pH gradients", Electrophoresis, 2000, vol. 21(6), pp. 1037-1053.
Gorkin et al., "Centrifugal microfluidics for biomedical applications", Lab on a Chip, 2010, vol. 10, pp. 1758-1773.
Gusev et al., "Capillary columns with in situ formed porous monolithic packing for micro high-performance liquid chromatography and capillary electrochromatography", Journal of Chromatography A, 1999, vol. 855(1), pp. 273-290.
Harboe et al., "The 38-kDa protein of Mycobacterium tuberculosis: a review", Journal of Infectious Disease, 1992, vol. 166(4), pp. 874-884.
Hatch et al., "Integrated preconcentration SDS-PAGE of proteins in microchips using photopatterned cross-linked polyacrylamide gels", Analytical Chemistry, 2006, vol. 78(14), pp. 4976-4984.
Herr et al., "Microfluidic immunoassays as rapid saliva-based clinical diagnostics", Proceedings of the National Academy of Science USA, 2007, vol. 104(13), pp. 5268-5273.
Herr et al., "On-chip coupling of isoelectric focusing and free solution electrophoresis for multidimensional separations", Analytical Chemistry, 2003, vol. 75(5), pp. 1180-1187.
Hoffmann et al., "Direct comparison of GeneXpert MTB/RIF (Cepheid) with probeTEC (Becton-Dickinson) and Taqman MTB (Roche) for detection of TB bacteria", Pneumologie, 2012, vol. 66, Abstract P351 (1 p.).
Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.
Holmes et al., "Leukocyte analysis and differentiation using high speed microfluidic single cell impedance cytometry", Lab on a Chip, 2009, vol. 9, pp. 2881-2889.
Huang et al., "The primary structure of Staphylococcal enterotoxin B: III. The cyanogen bromide peptides of reduced and aminoethylated enterotoxin B, and the complete amino acid sequence", Journal of Biological Chemistry, 1970, vol. 245(14), pp. 3518-3525.
Huang et al., "Microfabrication of a tapered channel for isoelectric focusing with thermally generated pH gradient", Electrophoresis, 2002, vol. 23(20), pp. 3504-3510.
Invitrogen Life Technologies, "ZOOM IEF Fractionator, Instructional Manual", Catalog Nos. ZF10001 & ZF10002, Version C, Jul. 2004 (64 pp.).
IVD Technology, "Microfluidic applications for IVDs", DX Directions, 2010, Spring, pp. 6.
Jung et al., "The Mycobacterial 38kKilodalton glycolipoprotein antigen activates the mitogen-activated protein kinase pathway and release of proinflammatory cytokines through toll-like receptors 2 and 4 in human monocytes", Infection and Immunity, 2006, vol. 74(5), pp. 2686-2696.
Khawcharoenporn et al., "Tuberculin skin test and QuantiFERON-TB gold In-tube test for latent tuberculosis in Thai HIV-infected adults", Respirology, 2015, vol. 20, pp. 340-347.
Kim et al., "Fully integrated lab-on-a-disc for nucleic acid analysis of food-borne pathogens", Analytical Chemistry, 2014, vol. 86, pp. 3841-3848.
Koh et al., "Centrifugal microfluidic platform for ultrasensitive detection of botulinum toxin", Analytical Chemistry, 2015, vol. 81, pp. 922-928.
Landowski et al., "Combinatorial use of antibodies to secreted mycobacterial proteins in a host immune system-independent test for tuberculosis", Journal of Clinical Microbiology, 2001, vol. 39(7), pp. 2418-2424.
Lee et al., "A fully automated immunoassay from whole blood on a disc", Lab on a Chip, 2009, vol. 9(11), pp. 1548-1555.
Lee et al., "Fully integrated lab-on-a-disc for simultaneous analysis of biochemistry and immunoassay from whole blood", Lab on a Chip, 2011, vol. 11(1), pp. 70-78.
Li et al., "Epidemiology of HIV-associated tuberculosis in Urumqi, China", Transplantation Proceedings, 2015, vol. 47(8), pp. 2456-2459.
Lim et al., "Bead-based microfluidic immunoassays: The next generation", Biosensors and Bioelectronics, 2007, vol. 22(7), pp. 1197-1204.
Lim et al., "Rapid isoelectric trapping in a micropreparative-scale multicompartment electrolyzer", Electrophoresis, 2007, vol. 28(12), pp. 1851-1859.
Litvinov et al., "Centrifugal microfluidic platform for rapid, multiplexed detection of TB and HIV biomarkers in whole blood samples", Journal of Bioengineering & Biomedical Science, 2017, vol. 7(2), Article 1000230 (8 pp.).
Litvinov et al., "Centrifugal sedimentation immunoassays for multiplexed detection of enteric bacteria in ground water", Biomicrofluidics, 2016, vol. 10, Article 014103 (9 pp.).
Liu et al., "Quantification of circulating Mycobacterium tuberculosis antigen peptides allows rapid diagnosis of active disease and treatment monitoring", Proceedings of the National Academy of the Sciences of the United States of America, 2017, vol. 114(15), pp. 3969-3974.
Lo et al., "Photopolymerized diffusion-defined polyacrylamide gradient gels for on-chip protein sizing", Lab on a Chip, 2008, vol. 8(8), pp. 1273-1279.
Lo et al., "Plasma DNA as a prognostic marker in trauma patients", Clinical Chemistry, 2000, vol. 46(3), pp. 319-323.
Long et al., "Integration of nanoporous membranes for sample filtration/preconcentration in microchip electrophoresis", Electrophoresis, 2006, vol. 27(24), pp. 4927-4934.
Madou et al., "Lab on a CD", Annual Review of Biomedical Engineering, 2006, vol. 8, pp. 601-628.
Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.
McBain et al., "Polyethyleneimine functionalized iron oxide nanoparticles as agents for DNA delivery and transfection", Journal of Material Chemistry, 2007, vol. 17(24), pp. 2561-2565.

(56) References Cited

OTHER PUBLICATIONS

McNerney et al., "Towards a point-of-care test for active tuberculosis: obstacles and opportunities", Nature Reviews Microbiology, 2011, vol. 9, pp. 204-213.
Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.
Min et al., "Functional integration of DNA purification and concentration into a real time micro-PCR chip", Lab on a Chip, 2011, vol. 11(2), pp. 259-265.
Moen et al., "A centrifugal microfluidic platform that separates whole blood samples into multiple removable fractions due to several discrete but continuous density gradient sections", PLoS One, 2017, vol. 11, Article e0153137 (11 pp.).
Ní Cheallaigh et al., "Interferon gamma release assays for the diagnosis of latent TB infection in HIV-infected individuals in a low TB burden country", PLoS One, 2013, vol. 8, Article e53330 (7 pp.).
O'Farrell, "High resolution two-dimensional electrophoresis of proteins", Journal of Biological Chemistry, 1975, vol. 250(10), pp. 4007-4021.
Ogle et al., "Preparative-scale isoelectric trapping separations using a modified Gradiflow unit", Journal of Chromatography A, 2002, vol. 979(1-2), pp. 155-161.
Ottenhoff et al. "Novel human immunodeficiencies reveal the essential role of type-1 cytokines in immunity to intracellular bacteria", Immunology Today, 1998, vol. 19, pp. 491-494.
Owiti, "Local knowledge of the link between tuberculosis and HIV-1/AIDS among the Turkana of Lodwar township: implications for tuberculosis and HIV-1/AIDS prevention", World Health & Population, 2008, vol. 10(3), pp. 36-46.
Pandie et al., "Diagnostic accuracy of quantitative PCR (Xpert MTB/RIF) for tuberculous pericarditis compared to adenosine deaminase and unstimulated interferon-γ in a high burden setting: A prospective study", BMC Medicine, 2014, vol. 12, Article 101 (11 pp.).
Pathak et al., "Effects of in vitro HIV-1 infection on mycobacterial growth in peripheral blood monocyte-derived macrophages", Infection and Immunology, 2010, vol. 78, pp. 4022-4032.
Pathakumari et al., "Dynamic IgG antibody response to immunodominant antigens of M. tuberculosis for active TB diagnosis in high endemic settings", Clinica Chimica Acta, 2016, vol. 461, pp. 25-23.
Phaneuf et al., "Portable centrifugal microfluidic system for diagnostics in resource-limited settings", IEEE Healthcare Innovation Point-Of-Care Technologies Conference (HI-POCT), Nov. 9-11, 2016, pp. 89-91.
Pooran et al., "Different screening strategies (single or dual) for the diagnosis of suspected latent tuberculosis: a cost effectiveness analysis", BMC Pulmonary Medicine, 2010, vol. 10, Article 7 (14 pp.).
Price et al., "Light-scattering immunoassay", in Principles and Practice Immunoassay (Second Ed., C.P. Price & D.J. Newman, eds.), 1997, Stockton Press (New York, NY), Chap. 18, pp. 445-480.
PubChem Entry for "TWEEN 20", retrieved on Oct. 4, 2016 from https://pubchem.ncbi.nlm.nih.gov/compound/Tween_20#section=Names-and-identifiers (2 pp.).
PubChem Search results for "2,3-dihydroxypropyl octanoate", retrieved on Oct. 5, 2016 from https://www.ncbi.nlm.nih.gov/pcompound/?term=2%2C3-dihydroxypropyl+octanoate (4 pp.).
Qiu et al., "Spin-valve based magnetoresistive nanoparticle detector for applications in biosensing", Sensors and Actuators A: Physical, 2017, vol. 25, pp. 174-180.
Raja et al., "Improved diagnosis of pulmonary tuberculosis by detection of free and immune complex-bound anti-30kDa antibodies", Diagnostic Microbiology and Infectious Disease, 2004, vol. 50(4), pp. 253-259.
Ramos et al., "Contribution of interferon gamma release assays testing to the diagnosis of latent tuberculosis infection in HIV-infected patients: a comparison of QuantiFERON-TB Gold in Tube, T-SPOT.TB and tuberculin skin test", BMC Infectious Diseases, 2012, vol. 12, Article 169 (10 pp.).
Rhodes et al., "Plasma DNA concentration as a predictor of mortality and sepsis in critically ill patients", Critical Care, 2006, vol. 10(2), Article R60 (pp. 1-7).
Riahi et al., "Molecular detection of bacterial pathogens using microparticle enhanced double-stranded DNA probes", Analytical Chemistry, 2011, vol. 83(16), pp. 6349-6354 and Supporting Information (8 pp.).
Rider et al., "A B cell-based sensor for rapid identification of pathogens", Science, 2003, vol. 301, pp. 213-215.
Riegger et al., "Read-out concepts for multiplexed bead-based fluorescence immunoassays on centrifugal microfluidic platforms", Sensors and Actuators A—Physical, 2006, vol. 126, pp. 455-462.
Righetti, "The Alpher, Bethe and Gamow of IEF, the alpha-Centaury of electrokinetic methodologies—part II: immobilized pH gradients", Electrophoresis, 2007, vol. 28(4), pp. 545-555.
Righetti, "The Alpher, Bethe, Gamow of isoelectric focusing, the alpha-Centaury of electrokinetic methodologies—part I", Electrophoresis, 2006, vol. 27(5-6), pp. 923-938.
Saukkonen et al., "Cell-free plasma DNA as a predictor of outcome in severe sepsis and septic shock", Clinical Chemistry, 2008, vol. 54(6), pp. 1000-1007.
Schaff et al., "Whole blood immunoassay based on centrifugal bead sedimentation", Clinical Chemistry, 2011, vol. 57(5), pp. 753-761.
Schembri et al., "Portable simultaneous multiple analyte whole-blood analyzer for point-of-care testing", Clinical Chemistry, 1992, vol. 38(9), pp. 1665-1670.
Schneider et al., "Characterization of EBV-genome negative "null" and "t" cell lines derived from children with acute lymphoblastic leukemia and leukemic transformed non-Hodgkin lymphoma", International Journal of Cancer, 1977, vol. 19(5), pp. 621-626.
Sigma-Aldrich product page for TWEEN 20, archived from Jun. 28, 2012, retrieved on Oct. 5, 2016 from https://web.archive.org/web/20120628080753/http://www.sigmaaldrich.com/catalog.product/sial/p1379?ang=en&region= (43 pp.).
Sommer et al., "On-chip isoelectric focusing using photopolymerized immobilized pH gradients", Analytical Chemistry, 2008, vol. 80(9), pp. 3327-3333.
Steingart et al., "Performance of purified antigens for serodiagnosis of pulmonary tuberculosis: a meta-analysis", Clinical and Vaccine Immunology, vol. 16(2), pp. 260-276.
Sultan et al., "Comparison of two interferon-gamma release assays (QuantiFERON-TB Gold In-Tube and T-SPOT.TB) in testing for latent tuberculosis infection among HIV-infected adults", International Journal of STD & AIDS, 2013, vol. 24(10), pp. 775-779.
Suzuki et al., "Experimental optimization of probe length to increase the sequence specificity of high-density oligonucleotide microarrays", BMC Genomics, 2007, vol. 8, Article 373 (13 pp.).
Tan et al., "Miniaturized capillary isoelectric focusing in plastic microfluidic devices", Electrophoresis, 2002, vol. 23(20), pp. 3638-3645.
Tasbiti et al., "MDR-TB antibody response (western blot) to fractions of isoniazid and rifampicin resistant antigens of Mycobacterium tuberculosis", Current Microbiology, 2015, vol. 71(6), pp. 638-642.
Uma Devi et al., "Antibody response to Mycobacterium tuberculosis 30 and 16kDa antigens in pulmonary tuberculosis with human immunodeficiency virus coinfection", Diagnostic Microbiology and Infectious Disease, 2003, vol. 46(3), pp. 205-209.
Wang et al., "The Abbott RealTime MTB assay and the Cepheid GeneXpert assay show comparable performance for the detection of Mycobacterium tuberculosis in sputum specimens", International Journal of Infectious Diseases, 2016, vol. 45, pp. 78-80.
Wood et al., "Risk factors for developing tuberculosis in HIV-1-infected adults from communities with a low or very high incidence of tuberculosis", Journal of Acquired Immune Deficiency Syndromes, 1999, vol. 23(1), pp. 75-80.
Young et al., "Confronting the scientific obstacles to global control of tuberculosis", Journal of Clinical Investigation, 2008, vol. 118(4), pp. 1255-1265.

(56) References Cited

OTHER PUBLICATIONS

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Zhang et al., "Mycobacterium tuberculosis secreted proteins as potential biomarkers for the diagnosis of active tuberculosis and latent tuberculosis infection", Journal of Clinical Laboratory Analysis, 2015, vol. 29, pp. 375-382.

Zhou et al., "Protein array identification of protein markers for serodiagnosis of Mycobacterium tuberculosis infection", Scientific Reports, 2015, vol. 5, Article 15349 (10 pp.).

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemistry, 2000, vol. 284(2), pp. 266-278.

US 10,786,811 B1

DETECTION OF ACTIVE AND LATENT INFECTIONS WITH MICROFLUIDIC DEVICES AND SYSTEMS THEREOF

CROSS-REFERENCE TO RELATED APPLICATION

This application claims the benefit of U.S. Provisional Application No. 62/412,153, filed Oct. 24, 2016, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates, in part, to methods of detecting one or more targets of interest in a sample. In one instance, the target can be correlated to an active infection (e.g., by a virus and/or a bacterium). Methods can include treating the sample with a dissociation agent, thereby releasing the target of interest for more accurate detection (e.g., by use of a sedimentation-based centrifugal microfluidic devices). Also described herein are microfluidic devices and systems for use with a dissociation agent.

BACKGROUND OF THE INVENTION

Multiplexed detection of biomarkers can provide key insights into patient diagnosis and treatment. Miniaturized diagnostic platforms can be particularly useful if biomarker detection is accompanied by minimal sample preparation, rapid turnaround time, and simplicity of use. At times, diagnostic tests can require some degree of sample pre-treatment to ensure that the appropriate target of interest can be detected in a sensitive and specific manner for a particular diagnosis (e.g., an active infection requiring treatment or a latent, past infection requiring no medical treatment). It can be particularly beneficial if such pre-treatment of a sample, when required, can be automated within the diagnostic platform.

SUMMARY OF THE INVENTION

The present invention, in part, relates to methods of detecting a target of interest, in which the method requires treatment with a dissociation agent to facilitate detection of the target. In one non-limiting example, the target of interest can be bound to a host-responsive protein, thereby limiting the sensitivity of target detection. By treating the sample with a dissociation agent (e.g., thereby releasing viral proteins from host-responsive human antibodies), target detection can be conducted in a sensitive manner. Accordingly, described herein are methods, microfluidic devices, and systems that allow for detecting target(s) of interest after treatment with a dissociation agent. In some instances, the exemplary microfluidic device is configured to transport particles (that are attached to the target of interest) by way of sedimentation forces.

In one non-limiting instance, the methods herein allow for simultaneous detection of a plurality of targets of interest (e.g., a target indicative of past or present viral infection and another target indicative of past or present bacterial infection). In some embodiments, the targets of interest are indicative of an active or latent infection by *M. tuberculosis* and indicative of an infection by a human immunodeficiency virus (HIV).

In a first aspect, the invention features a method including: providing a mixture including a sample treated with a dissociation agent; neutralizing the mixture with a neutralization agent, thereby providing a treated mixture including a neutralized, dissociated sample; layering the treated mixture on a density medium, where the treated mixture further includes a first population of beads; and subjecting the treated mixture to a sedimentation force such that the first population of beads, or a portion thereof, travels through the density medium.

In some embodiments, the neutralization agent is configured to neutralize the dissociation agent. In other embodiments, the density medium is disposed within a detection chamber that is disposed within a substrate (e.g., of a microfluidic device, such as any described herein).

In some embodiments, the first population of beads is characterized by a first density and/or a first radius. In other embodiments, the first population of beads is configured to bind to a first target of interest. In yet other embodiments, the treated mixture includes a second population of beads, in which the second population is optionally characterized by a second density and/or a second radius (e.g., where the second density is different than the first density and/or where the second radius is different than the first radius). In other embodiments, the second population of beads is configured to bind to a second target of interest (e.g., where the second target of interest is different than the first target of interest).

In some embodiments, the density medium is characterized by a density that is less than the first density of the first population of beads. In other embodiments, the density medium is characterized by a density that is less than the second density of the second population of beads. In yet other embodiments, the density medium is characterized by a density that is greater than the treated sample and less than the first density and/or the second density.

In some embodiments, the sample includes a host-responsive protein (e.g., an antibody) that binds to the target of interest (e.g., a first, second, third, etc., target of interest, including an antigen, such as a non-host protein). In further embodiments, the dissociation agent is configured to dissociate the host-responsive protein from the target of interest. Other non-limiting targets of interest are described herein (e.g., a non-host protein, a non-host nucleic acid, a host-responsive protein, a host-responsive nucleic acid, or a fragment thereof and/or a complex thereof).

In some embodiments, the sample includes a plurality of targets of interest. In further embodiments, the sample includes a plurality of host-responsive proteins that bind to the plurality of targets of interest (e.g., a first host-responsive protein that binds to its respective first target of interest, or a plurality of first host-responsive proteins that binds to its respective first target of interest, or a plurality of host-responsive proteins, in which one or more host-responsive proteins bind to a first target of interest). In other embodiments, the dissociation agent is configured to dissociate the plurality of host-responsive proteins from the plurality of targets of interest (e.g., configured to dissociate at least one of the plurality of host-responsive proteins from at least one of the plurality of targets of interest).

In other embodiments, the sample includes a non-host protein that binds to the target of interest. In some embodiments, the dissociation agent is configured to dissociate the non-host protein from the target of interest.

In some embodiments, the sample includes a plurality of targets of interest and a plurality of non-host proteins that bind to the plurality of targets of interest (e.g., a first non-host protein that binds to its respective first target of interest, or a plurality of non-host proteins that binds to its respective first target of interest, or a plurality of non-host protein, in which one or more host-responsive proteins bind to a first target of interest). In other embodiments, the dissociation agent is configured to dissociate the plurality of non-host proteins from the plurality of targets of interest.

In some embodiments, the sample includes the first target of interest indicative of a bacterial infection (e.g., *Mycobacterium* infection) and a second target of interest indicative of a viral infection (e.g., Retroviridae infection).

In some embodiments, the treated mixture (e.g., or a portion thereof) includes one or more components that is characterized by a density that is less than the density of the density medium. In other embodiments, the treated mixture further includes a second population of beads characterized by a second density that is different than the first density (e.g., where the second population of beads is further configured to bind to a second target of interest that is different from the first target of interest). In yet other embodiments, the treated mixture further includes a second population of beads characterized by a second radius that is different than the first radius (e.g., where the second population of beads is further configured to bind to a second target of interest that is different from the first target of interest). In other embodiments, the treated mixture further includes one or more detection agents configured to bind directly or indirectly to the first population of beads, or a portion thereof, if in the presence of the target of interest.

In some embodiments, said neutralizing further includes providing the treated mixture within a channel (e.g., a microchannel) or a chamber (e.g., a reservoir, a sample chamber, an incubation chamber, an assay chamber, a reaction chamber, a post-processing chamber, or any described herein) disposed within the substrate (e.g., of the microfluidic device). In other embodiments, said neutralizing further includes spinning the substrate to transport the neutralization agent through the channel and into the mixture within the reaction chamber.

In some embodiments, said layering further includes transporting the treated mixture to the detection chamber by way of a channel (e.g., a microchannel) disposed within the substrate (e.g., of the microfluidic device).

In some embodiments, said transporting and/or said subjecting includes spinning the substrate (e.g., of the microfluidic device).

In some embodiments, the method further includes: detecting a presence or absence of a signal from one or more detection agents bound directly or indirectly to a population of beads (e.g., a first population and/or a second population), or a portion thereof. In some embodiments, the method includes conducting a competitive assay.

In a second aspect, the present invention features a microfluidic device including: a substrate including a sample port (e.g., configured to receive a sample or a mixture including the sample); a main channel disposed, at least in part, within or on the substrate, where the main channel is in fluidic communication with the sample port; and an assay area disposed, at least in part, within or on the substrate, where the assay area is in fluidic communication with main channel that is configured to deliver the sample, or a portion thereof, into the assay area.

In some embodiments, the assay area includes a detection chamber, a density medium (e.g., disposed within the detection chamber), a reaction chamber, and a channel in fluidic communication with the detection chamber and the reaction chamber. In other embodiments, the reaction chamber is configured to contain a treated mixture (e.g., including a neutralized, dissociated sample and a first population of beads characterized by a first density and/or a first radius). In yet other embodiments, the first population of beads is configured to bind to a first target of interest. In some embodiments, the treated mixture includes a second population of beads (e.g., any described herein). In other embodiments, the channel is further configured to restrict transport of at least a portion of the sample through the density medium.

In some embodiments, the detection chamber is configured to transport the first population of beads, or a portion thereof, through the density medium when subjected to a sedimentation force (e.g., a centrifugal force).

In further embodiments, the device includes a chamber in fluid communication with the reaction chamber and/or the detection chamber. In some embodiments, the chamber is configured to store a dissociation agent, a neutralization agent, a capture agent, and/or a detection agent.

In a third aspect, the present invention features a system including a microfluidic disc (e.g., any device described herein); a motor module configured to be coupled to the microfluidic disc and to spin the microfluidic disc in response to a motor control signal; and a detection module configured to detect a signal from one or more detection agents present in the assay area. In some embodiments, the detection module is configured to generate an electronic detection signal based, at least in part, on the signal from the one or more detection agents.

In some embodiments, the microfluidic disc includes: a substrate including a sample port configured to receive a sample or a mixture including the sample; a main channel disposed, at least in part, within or on the substrate, where the main channel is in fluidic communication with the sample port; and an assay area disposed, at least in part, within or on the substrate, where the assay area is in fluidic communication with main channel that is configured to deliver the sample, or a portion thereof, into the assay area. In other embodiments, the assay area includes a detection chamber; a density medium disposed within the detection chamber; a reaction chamber configured to contain a treated mixture including a neutralized, dissociated sample and a first population of beads characterized by a first density and/or a first radius, where the first population of beads is configured to bind to a first target of interest; and a channel in fluidic communication with the detection chamber and the reaction chamber. In yet other embodiments, the detection chamber is configured to transport the first population of beads, or a portion thereof, through the density medium when subjected to a sedimentation force.

In further embodiments, the system includes a processing device coupled to the motor module and the detection module. In some embodiments, the processing device is configured to generate the motor control signal and provide the motor control signal to the motor module. In other embodiments, the processing device is further configured to receive the electronic detection signal from the detection module.

In any embodiment herein, the methods, devices, and/or systems employ a first population of beads is characterized by a first density and/or a first radius. In some embodiments, the first population of beads is configured to bind to a first target of interest. In other embodiments, the first population of beads is configured to bind to a second target of interest that is different from the first target of interest. In yet other embodiments, the first population of beads further includes one or more capture agents configured to bind the first target of interest, thereby forming a population of captured target-bead complexes. In further embodiments, the one or more detection agents is configured to bind to the population of captured target-bead complexes, or a portion thereof.

In any embodiment herein, the methods, devices, and/or systems employ a second population of beads, in which the second population is optionally characterized by a second density and/or a second radius (e.g., where the second density is different than the first density and/or where the second radius is different than the first radius). In some embodiments, the second population of beads is configured to bind to a second target of interest (e.g., where the second target of interest is different than the first target of interest).

In any embodiment herein, the methods, devices, and/or systems employ a density medium that is characterized by a density that is less than the first density of the first population of beads. In some embodiments, the density medium includes a plurality of components each characterized by a particular density or density range. In other embodiments, the density medium is characterized by a density that is less than the second density of the second population of beads. In yet other embodiments, the density medium is characterized by a density that is greater than the treated sample and less than the first density and/or the second density.

In any embodiment herein, the target of interest (e.g., the first target of interest) is a host-derived protein, a non-host derived protein, an antibody, an antigen, a peptide, a nucleic acid, a protein modified by a non-host pathogen (e.g., a protein biomarker, in which the modification by the non-host pathogen includes a change in the level of the biomarker in the host or in a sample from the host, as compared to a control sample that is not infected by the pathogen), a nucleic acid modified by a non-host pathogen (e.g., a nucleic acid biomarker, in which the modification by the non-host pathogen includes a change in the level of the biomarker in the host or in a sample from the host, as compared to a control sample that is not infected by the pathogen), or a cell modified by a non-host pathogen (e.g., a T-cell, in which the modification by the non-host pathogen includes a change in the level of the T-cell in the host or in a sample from the host, as compared to a control sample that is not infected by the pathogen; or a change in levels of cluster of differentiation marker levels in the host or in a sample from the host, as compared to a control sample that is not infected by the pathogen). Non-limiting, exemplary targets of interest include a protein (e.g., Ag85A protein, Ag85B protein, Ag85C protein, and/or 38-kDa protein), an antigen (e.g., p24 antigen, HIV-1 gp41 antigen, HIV-2 gp36 antigen, and/or gp120 antigen), etc., as well as any described herein.

In any embodiment herein, a first population of particles (e.g., having a first particle size and/or first particle density) can include a first type of capture agent (e.g., configured to bind the first target of interest). In some embodiments, a second population of particles (e.g., having a second particle size and/or second particle density) can include a second type of capture agent (e.g., configured to bind a second target of interest that is different than the first target of interest), thereby allowing for different sedimentation rates and/or separation zones for each population. Non-limiting, exemplary capture agents include an antibody, a nucleic acid, a particle, etc., as well as any described herein.

In any embodiment herein, the sedimentation force is generated by gravity and/or centrifugal force.

In any embodiment herein, the detection chamber is defined within a microfluidic disc.

In any embodiment herein, the microfluidic disc further includes a reaction chamber configured to receive the sample; and a channel configured to transport the dissociation agent and/or the neutralization agent to the reaction chamber that is in fluidic communication with the detection chamber.

Additional details follow.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

By "subject" or "host", which can be used interchangeably, is meant a human or non-human animal (e.g., a mammal). In some embodiments, the host can have or can be suspected of having an active or latent infection (e.g., an active or latent mycobacterial infection).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

(FIG. 1A); a non-limiting schematic of assay areas 1000, 1100 (FIG. 1B-1C); a first detection methodology for employing a capture antibody 13 to provide a detectable target-bead complex 19 (FIG. 1D); and another detection methodology for employing a capture agent 23 to provide a detectable target-bead complex 29 (FIG. 1E).

DETAILED DESCRIPTION OF THE INVENTION

The present invention relates to methods, devices, and systems for detecting one or more targets of interest in a sample. In one instance, the target of interest can form a complex within the sample, such that a dissociation agent can be used to disrupt that complex, which in turn enhances detection of the target. Furthermore, the method relies on the use of a density medium to effectively isolate the target of interest, thereby simplifying detection of the target. The methods, devices, and systems can be adapted for single detection of a target or for multiplexed detection of a plurality of targets, thereby enhancing selectivity and/or sensitivity of the assay.

Figure 1A:
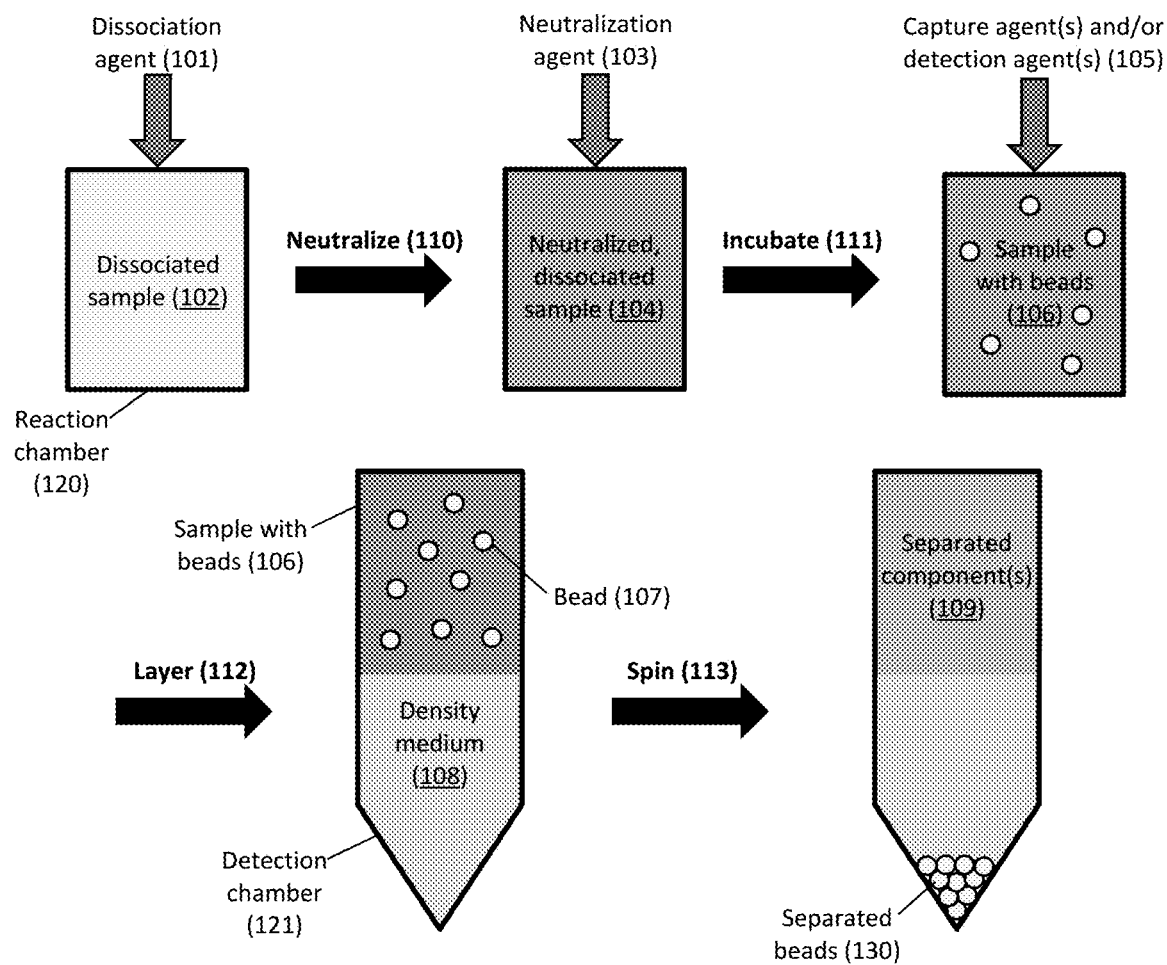
FIG. 1A-1E shows schematics of exemplary methods, assay areas, and detection methodologies. Provided are a non-limiting method for providing a neutralized, dissociated sample 104 for subsequent layering 112 and spinning 113

FIG. 1A provides an exemplary method, e.g., for performing an assay. The method can include providing a sample treated with a dissociation agent 101, thereby resulting in a dissociated sample 102. Next, neutralizing 110 the dissociated sample with a neutralization agent 103 results in a neutralized, dissociated sample 104. In some instances, the dissociation agent is an acidic agent, and the neutralization agent is a basic agent (or vice versa).

The sample can further include one or more beads, which can be provided at any useful step of the assay method or during any useful time while conducting the assay. In one instance, one or more beads are provided immediately after obtaining sample from the subject (e.g., in which the beads are provided in a collection tube employed to draw blood from a subject). In another instance, one or more beads are provided off-chip or on-chip (e.g., within the microfluidic device). In yet another instance, one or more beads are provided before, during, and/or after the dissociation step (e.g., providing a dissociation agent) and/or the neutralization step (e.g., providing a neutralization agent). In another instance, one or more beads are provided prior (e.g., immediately prior) to the layering step (e.g., providing a density medium). In one instance, one or more beads are provided prior (e.g., immediately prior) to the subjecting step (e.g., providing a density medium). When two or more different populations of beads are employed, then each population can be introduced to the sample (e.g., an initial sample; a dissociated sample; and/or a neutralized, dissociated sample) at the same time or at different times.

In one non-limiting embodiment, as seen in FIG. 1A, the method can include incubating 111 the sample with one or more capture agents and/or one or more detection agents 105. The incubating step can include a single stage of incubation with desired agents or multiple stages of incubation with one or more desired agents at each step. In one non-limiting instance, the incubation step includes incubating with one or more capture agents (e.g., attached to a bead or provided as a complex with a bead) and then incubating with one or more detection agents (e.g., for a time sufficient to allow binding of the detection to the target-bead complex). Additional details regarding the incubation step is described herein (see, e.g., FIG. 1D-1E).

After obtaining a sample with beads, the sample can be introduced to a density medium in any useful manner. Thus, in one instance, the method can include layering 112 a sample with beads 106 (e.g., any described herein, including any mixture herein having one or more beads 107) on a density medium 108.

Separation can be affected in any useful manner. In one instance, separation can include use of a sedimentation force (e.g., a centrifugal force) to propel particles through the density medium, in which the extent of separation can depend on one or more physical characteristics that affect fluid flow and fluid forces (e.g., such characteristics including particle density, particle size, particle geometry, etc.). In some embodiments, denser components will travel through the density medium, whereas less dense components (e.g., unreacted capture agents, unreacted detection agents, biological components of the sample such as cellular debris, buffer, unreacted agents and reagents, etc.) will remain within a bulk fluid separated from the density medium. In this way, a combination of the beads and the density medium provides effective separation of the targets to be detected.

Accordingly, in one non-limiting instance as in FIG. 1A, the method can further include spinning 113 the sample in proximity to the density medium 108, thereby providing one or more separated components 109 and separated beads 130.

Figure 3:
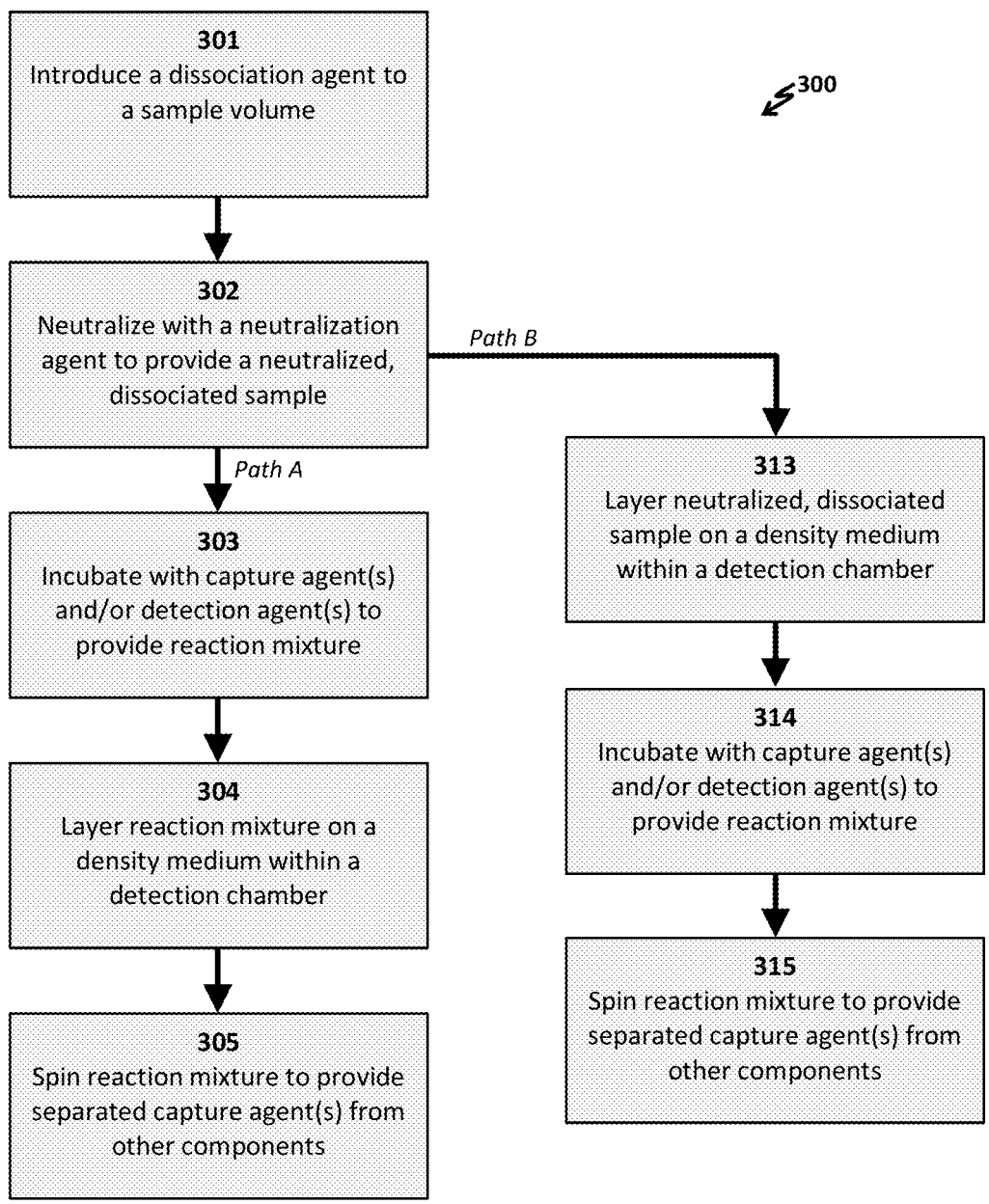
FIG. 3 shows an exemplary method 300 having two pathways (paths A and B) to provide separated capture agents.

FIG. 3 provides another exemplary method 300. As can be seen, the method 300 includes introducing 301 a dissociation agent to a sample volume (e.g., thereby providing a mixture) and then neutralizing 302 the sample with a neutralization agent to provide a reaction mixture (e.g., a neutralized, dissociated sample). After neutralization, any useful steps can be conducted in any useful manner to separate the sample or mixture. In one pathway (path A), the method can include incubating 303 the neutralized, dissociated sample with one or more capture agent(s) and/or one or more detection agent(s) to provide a reaction mixture (e.g., a neutralized, dissociated sample). Then, the resultant reaction mixture can be layered 304 on a density medium, e.g., disposed within a detection chamber. Finally, the reaction mixtures can be spun 305 to provide separated capture agent(s) from other components (e.g., bead complexes).

In another pathway (path B), the method can include layering 313 the mixture (e.g., the neutralized, dissociated sample) on a density medium, e.g., disposed within a detection chamber. Then, the mixture can be incubated 314 with one or more capture agent(s) and/or one or more detection agent(s) to provide a reaction mixture. Finally, the resultant reaction mixture can be spun 315 to provide separated capture agent(s) from other components (e.g., bead complexes).

The methods herein can be implemented in any useful device (e.g., a microfluidic device). As seen in FIG. 1A, the device can include a chamber (e.g., a reaction chamber 120) configured to store a sample (e.g., a dissociated sample 102, a neutralized, dissociated sample 104, and/or a sample with beads 106). The same chamber can be employed for each step, or a different chamber can be employed for at least one step (e.g., each and every step). When the same chamber is employed, then agents can deliver to that chamber (e.g., by way of one or more channels, vias, valves, etc.). When a different chamber is employed, then the agent can be pre-stored within that chamber and/or delivered to that chamber (e.g., by way of one or more channels, vias, valves, etc.).

As also seen in FIG. 1A, the device can include a separate chamber configured to include a density medium, e.g., a detection chamber 121. The detection chamber can be pre-loaded with a density medium. Alternatively, the density chamber can be configured to receive a density medium, e.g., by way of a channel, valve, via, etc. The geometry and volume of the detection chamber can be configured to promote separation, signal detection, etc. In one non-limiting instance, the detection chamber can be tapered at one end (e.g., located in proximity to a periphery of a microfluidic disc).

Figure 1B:
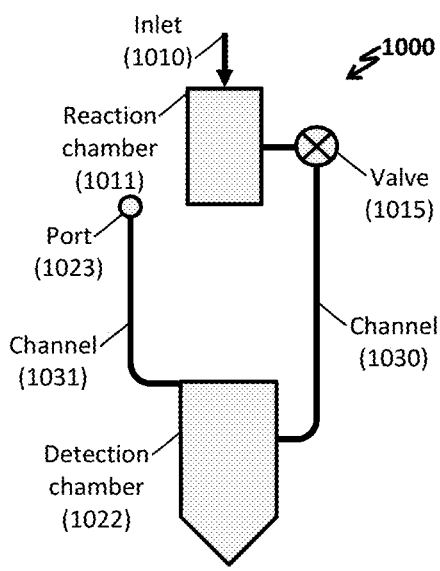
Figure 1C:
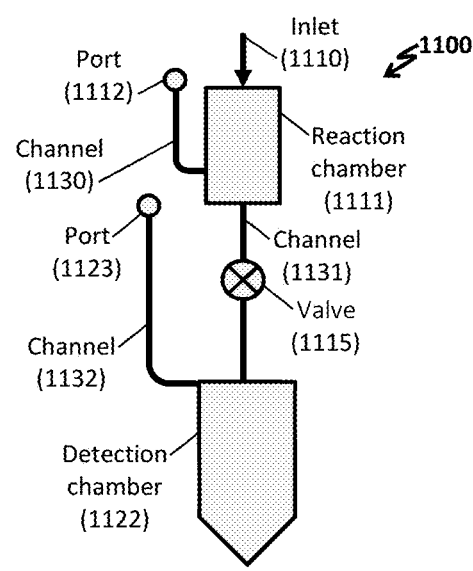

Any useful structure can be provided in the device. In one non-limiting instance, the device can include an assay area, which can be any useful area that facilitates one or more reaction(s), separation(s), and/or detection of a desired target. FIG. 1B-1C provides exemplary structures for an assay area 1000, 1100. In some embodiments as in FIG. 1B, the assay area 1000 includes a reaction chamber 1011 in fluidic communication with a detection chamber 1022. The chambers can be in fluidic communication with any other fluidic structures, such as a valve to control fluidic flow (e.g., direction of flow, extent of flow, etc.), an inlet (e.g., configured to introduce a sample, an agent, etc.), a port (e.g., configured to release pressure or fluid overflow), and/or a channel (e.g., to provide fluidic communication).

As seen in FIG. 1B, in one embodiment, the assay area 1000 includes an inlet 1010 in fluidic communication with the reaction chamber 1011, where the inlet is configured to deliver a sample to the reaction chamber; a first channel 1030 to provide fluidic communication between the reaction chamber 1011 and the detection chamber 1022, where a valve 1015 is optionally disposed in fluidic communication with the first channel 1030 to control fluid flow; and a port 1023 to provide release of pressure within any chamber, in which a second channel 1031 provides fluidic communication between the detection chamber 1022 and the port 1023.

As seen in FIG. 1C, in one embodiment, the assay area 1100 includes an inlet 1110 in fluidic communication with the reaction chamber 1111, where the inlet is configured to deliver a sample to the reaction chamber; a first port 1112 to provide release of pressure within any chamber, in which a first channel 1130 provides fluidic communication between the reaction chamber 1111 and the port 1112; a second channel 1131 to provide fluidic communication between the reaction chamber 1111 and the detection chamber 1122, where a valve 1115 is optionally disposed in fluidic communication with the second channel 1131 to control fluid flow; and a second port 1123 to provide release of pressure within any chamber, in which a third channel 1132 provides fluidic communication between the detection chamber 1122 and the port 1123.

Any useful capture and detection methodologies can be employed, e.g., within the method and/or the device. Based on the desired target of interest, the capture agent can be chosen to bind (e.g., selectively and/or specifically bind) the target. For instance, if the target is a protein, then the capture agent can be another protein that binds the protein target. In one embodiment, the target can be an antigen, and the capture agent can be an antibody that binds that antigen. In another embodiment, the target can be an antibody, and the capture agent can be an antigen that binds that antibody. In another instance, the target and capture agent are selected from a reactive pair (e.g., an antibody-antigen pair, a cross-linker reaction pair, a binding reaction pair, or a click-chemistry reaction pair); or a portion of the target and capture agent includes a reactive pair (e.g., an antibody-antigen pair, a cross-linker reaction pair, a binding reaction pair, or a click-chemistry reaction pair).

Figure 1D:
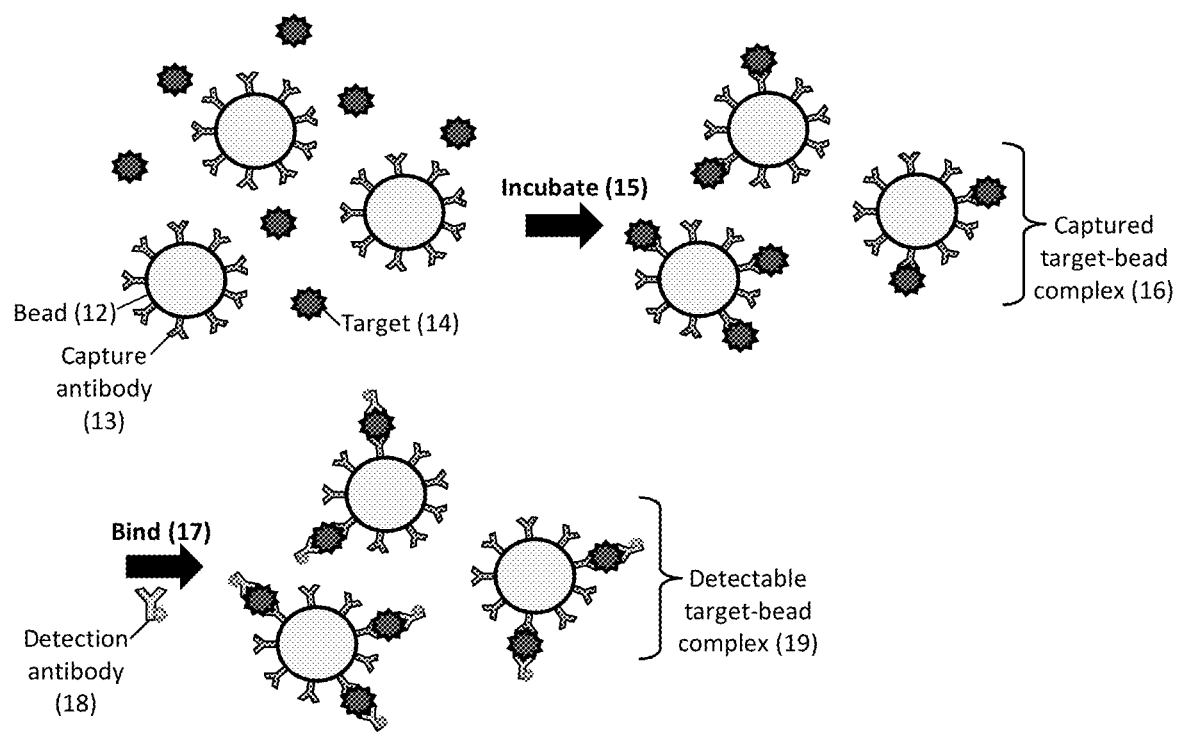

FIG. 1D provides one exemplary capture and detection methodology. As can be seen, the sample can include a target 14 that is a protein antigen. To capture this target, beads are employed, in which the bead 12 includes one or more capture agents 13 that is a capture antibody disposed on a surface of the bead. The capture antibody can be linked to the bead in any useful manner, e.g., by use of one or more reaction pairs between the antibody and the bead. After incubating 15 the sample with the bead 12, captured target-bead complexes 16 will be formed if the desired target is present in the sample. At times, the target may be present within the sample but bound within a complex, in which case a dissociation agent can be employed to release the target from the complex, thereby allowing the target to bind the capture agent.

Detection of the captured complex can be accomplished in any useful manner (e.g., by use of a primary antibody conjugate as in a direct assay, by use of a secondary antibody conjugate as in an indirect assay or a capture sandwich assay, by use of an enzymatic substrate, etc.). As can be seen in FIG. 1D, detection can include binding 17 the complex 16 with a detection agent configured to bind the target, thereby resulting in a detectable target-bead complex 19. In one instance, the detection agent is a detection antibody 18.

Figure 1E:
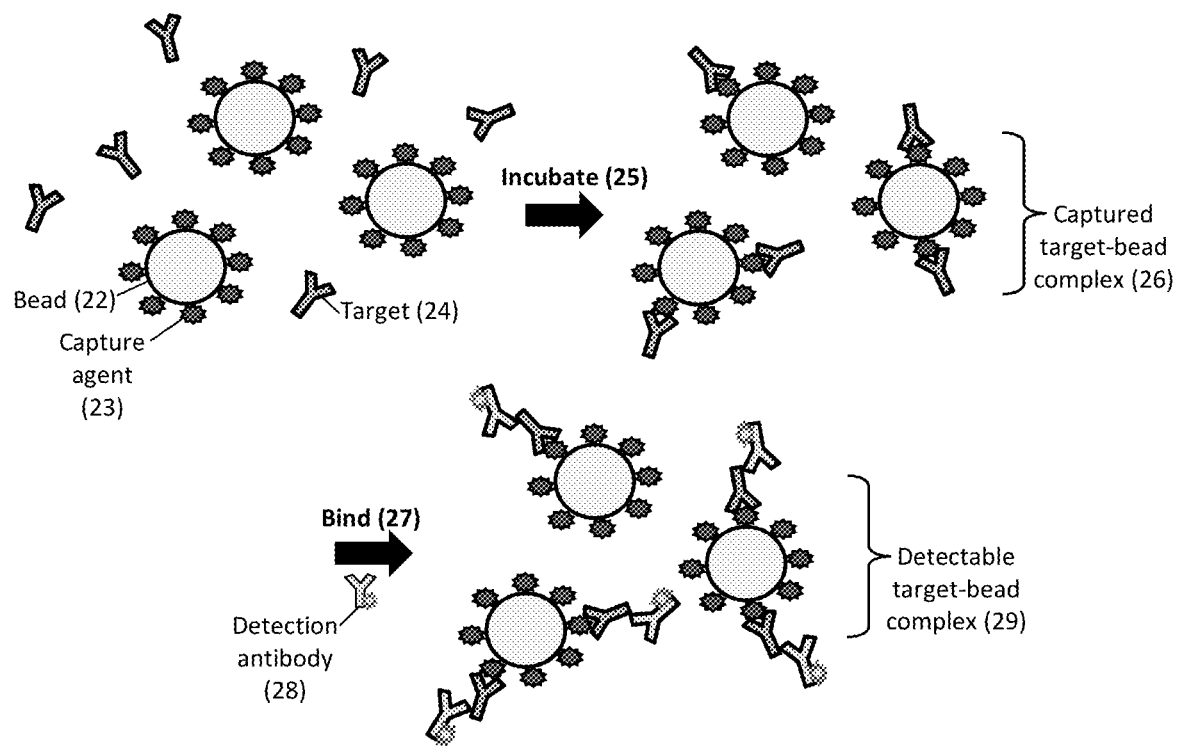

FIG. 1E provides another exemplary capture and detection methodology. As can be seen, the sample can include a target 24 that is a protein antibody. To capture this target, the bead 22 includes one or more capture agents 23 that is a capture antigen disposed on a surface of the bead. The capture antigen can be linked to the bead in any useful manner, e.g., by use of one or more reaction pairs between the antigen and the bead. After incubating 25 the sample with the bead 22, captured target-bead complexes 26 will be formed if the desired target is present in the sample. At times, a dissociation agent can be employed. Detection can include binding 27 the complex 26 with a detection agent configured to bind the target, thereby resulting in a detectable target-bead complex 29. In one instance, the detection agent is a detection antibody 28.

Each bead within a population can have the same capture agent. In some embodiments, each bead has the same surface concentration of capture agents or different surface concentrations can be employed. Furthermore, each population can have the same capture agent or different capture agents. For each capture agent, the same or different detection agent can be employed. In one instance, each detection agent can be associated with a distinguishable detectable signal, such that a distinct signal (e.g., a particular fluorescence signal at a particular emission wavelength) can distinguish one target from another target.

Figure 2:
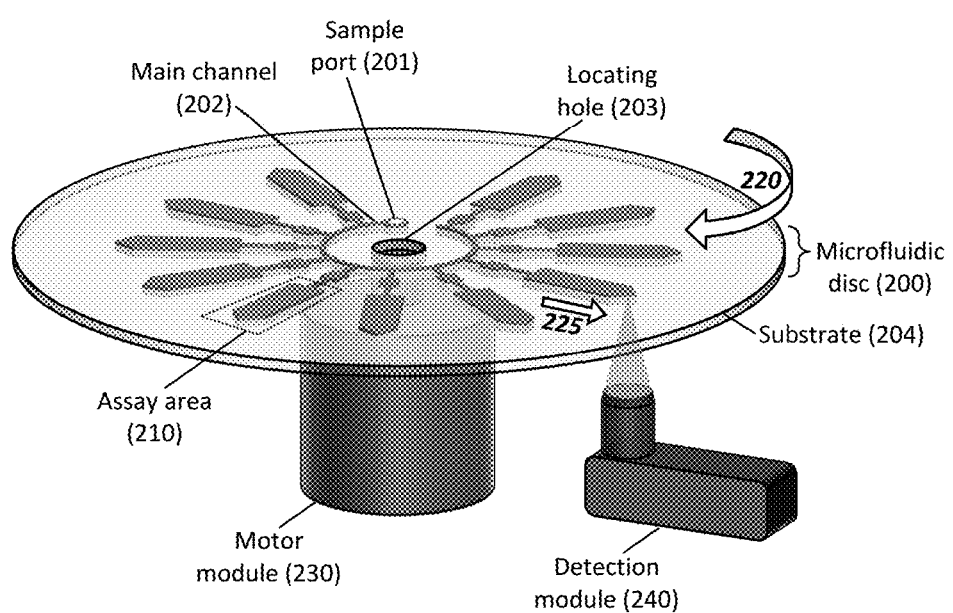
FIG. 2 shows an exemplary system including a microfluidic disc 200, a motor module 230, and a detection module 240.

The present invention also encompasses a device, which can be optionally employed with any useful system (e.g., any described herein). In one non-limiting instance, as seen in FIG. 2, the device is a microfluidic disc 200 including a substrate 204 having at least one sample port 201, e.g., configured to receive a sample, including a mixture including a sample portion. Any useful fluidic structure can be employed to provide fluidic communication, including a main channel 202 disposed within the substrate 204 and in fluidic communication with the sample port 201. The main channel 202, in turn, can be in fluidic communication with any useful assay area 210 (e.g., any described herein).

The device can be used in conjunction with a system. In one embodiment, as in FIG. 2, the device includes a locating hole 203 configured to be coupled to a portion of a motor module 230. The motor module, in turn, can be configured to spin 220 the device, thereby eliciting a sedimentation force 225 within the assay area 210. The system can further include a detection module 240 configured to detect a signal from one or more detection agents present in the assay area.

Target(s) of Interest and Multiplexed Detection

The present invention relates to methods and systems for detecting any useful target(s) of interest. In particular embodiments, the target of interest is present within the sample but is bound within a complex. The complex can be formed of any protein, such as a complex including a plurality of non-host proteins (e.g., as in the *M. tuberculosis* Ag85 complex having proteins Ag85A, Ag85B, and Ag85C) or a complex including a non-host protein with a host protein (e.g., as in a complex including the host-responsive anti-Ag85 antibody bound to the *M. tuberculosis* Ag85 complex or a portion thereof). In such an instance, a dissociation agent is employed to effectively release the target of interest, thereby allowing detection of the presence of this target. These methods and systems can be extended for multiplexed detection, in which the detection of more than one, different targets allows for enhanced testing (e.g., enhanced diagnosis of a disease or disease state in a specific and/or sensitive manner).

In one embodiment, the sample includes a host-responsive protein that binds to the first target of interest, in which the dissociation agent is configured to dissociate the host-responsive protein from the first target of interest. Exemplary dissociation agents and neutralization agents are described herein. Each sample can include one or more targets of interest and optionally, one or more host-responsive proteins for at least one target. In other embodiments, the sample can include one or more non-host proteins, in which at least one non-host protein can be the target of interest.

The target of interest can be host-derived (e.g., a host-responsive protein, such as an antibody against a non-host antigen; or a host-derived nucleic acid, or a complement thereof, including fragments of any of these) or non-host-derived (e.g., a non-host antigen, such as a bacterial antigen or a viral antigen; a non-host protein or peptide; or a non-host nucleic acid, or a complement thereof, including fragments of any of these). As used herein, in some embodiments, a "host" pertains to the subject from which a sample is obtained, and a "non-host" pertains to a foreign, exogenous entity. The target of interest can be an antibody, an antigen, a protein, a peptide, or a nucleic acid, as well as fragments, recombinant forms, and/or modified forms thereof, in which any of these can be host-derived, non-host-derived, or synthesized in vivo or in vitro.

In one non-limiting instance, the target of interest can include an antigen or an antibody against that antigen. For example, if the sample includes a target of interest that is a non-host antigen (e.g., a bacterial antigen), then the first population of beads is configured to bind to that non-host antigen (e.g., by including an antibody that binds to that non-host antigen). In another example, if the sample includes a target of interest that is a host-responsive protein (e.g., a host-responsive antibody against a non-host antigen, such as a host-responsive antibody against the bacterial antigen), then the first population of beads is configured to bind to that host-responsive protein (e.g., by including an antigen that binds to that host-responsive antibody). In one non-limiting example, if the target of interest is antigen 85 (Ag85) from *M. tuberculosis*, then the bead can include an anti-Ag85 antibody to bind to that antigen. Conversely, if the target of interest is the anti-Ag85 antibody present in the sample as a host-derived protein produced endogenously by the host's immune system in response to tuberculosis infection, then the bead can include the Ag85 antigen that binds to that host-responsive anti-Ag85 antibody protein. Other detection modalities employing antigen-antibody pairs would be apparent to a skilled artisan.

In one instance, the target of interest is correlated with the identification of a bacterial infection (e.g., a tuberculosis infection, including a latent or active infection caused by *Mycobacterium tuberculosis* (*M. tuberculosis*) in a human subject or host, an infection caused by *Mycobacterium bovis* (*M. bovis*) in cattle, or an infection caused by nontuberculous mycobacteria, e.g., *M. leprae, M. avium*, and *M. kansasii*). Such an infection may be present with any one or more comorbid disease states, such as a viral infection (e.g., an infection with the human immunodeficiency virus (HIV), a hepatitis B virus, or a hepatitis C virus), a parasitic infection (e.g., an infection with a helminth, a protozoon, and/or an ectoparasite), a metabolic disease (e.g., diabetes), or a pulmonary disease (e.g., chronic obstructive pulmonary disease (COPD) or silicosis). As such, a target of interest may also include any useful agent indicative of the presence or absence of any of these comorbid disease states. Exemplary targets of interest include an antigen (e.g., provided by a non-host, such as a viral protein or a bacterial protein), an antibody (e.g., a host-derived antibody that is responsive to a non-host antigen, or an antibody raised against the non-host antigen, a fragment thereof, or a recombinant form of any of these), a cytokine (e.g., correlated with the presence of an infection, such as a bacterial infection and/or a viral infection), a biomarker (e.g., correlated with the presence of an infection, such as a bacterial infection and/or a viral infection), as well as multiplexed combinations of any of these.

In particular, patient populations with an immunocompromising disease (e.g., such as an HIV infection) are at high risk for contracting a tuberculosis infection and for conversion of a latent form of the disease to an active infection. Early diagnosis of tuberculosis in such patients can minimize health complications. In one aspect, the present invention relates to methods and systems that are configured to detect the absence or presence of a causative agent of tuberculosis and a causative agent of a viral infection (e.g., an HIV infection or a hepatitis infection). Exemplary causative agents include any target of interest described herein, as well as antigens, antibodies, cytokines, and biomarkers (e.g., CXCL10 (IP-10), IL-1β, IL-2, IL-4, IL-5, IL-6, IL-9, IL-10, IL-12p70, IL-13, IL-17A, IL-22, IFN-α, IFN-γ, sCD40L, TNF-α, and/or vascular endothelial growth factor A (VEGF-A)) indicative of the presence of the causative agent of tuberculosis or a viral infection. Non-limiting, exemplary targets of interest (and agents for binding such targets) for HIV include the HIV virus, a viral protein antigen (e.g., p24 antigen), an envelope glycoprotein antigen (e.g., HIV-1 gp41, HIV-2 gp36, gp120), an HIV-derived nucleic acid (e.g., HIV-1 RNA or a complement thereof), and/or an anti-HIV antibody (e.g., a host-responsive anti-HIV-1 IgM antibody produced by as an immunological response to a past or present HIV-1 infection), as well as corresponding antigens/antibodies of any of these; targets of interest (and agents for binding such targets) for hepatitis virus include the virus itself (e.g., hepatitis B virus (HBV) or hepatitis C virus (HCV)), a viral surface protein (e.g., hepatitis B surface antigen (HBsAg)), a viral core protein (e.g., hepatitis C core antigen (HCc) or hepatitis B core antigen (HBc)), a virus-derived nucleic acid (e.g., HCV RNA or a complement thereof), a nonstructural protein (e.g., NS3, NS4, or NS5 for HCV), and/or an anti-viral antibody (e.g., a host-responsive anti-HCV IgM antibody produced by as an immunological response to an HCV infection, or a host-responsive anti-HBsAg antibody produced by as an immunological response to a past or present HBV infection or vaccination, or a host-responsive anti-HBc antibody produced as an immunological response to a past or present HBV infection), as well as corresponding antigens/antibodies of any of these.

Drug-resistant tuberculosis is an emerging threat. In some embodiments, the target of interest is a drug-resistant strain of the causative bacterium, and the plurality of beads is configured to bind to that strain. Exemplary drug-resistant strains include multi-drug resistant tuberculosis (MDR-TB), isoniazid-resistant tuberculosis, or rifampicin-resistant tuberculosis. In some non-limiting instances, the bead includes an antibody that binds to a domain of the strain that distinguished the drug-resistant strain from the drug-sensitive strain. Non-limiting antibodies and methods for identifying and isolating such antibodies are described in Hadizadeh Tasbiti A H et al., "MDR-TB antibody response (Western Blot) to fractions of isoniazid and rifampicin resistant antigens of *Mycobacterium tuberculosis*," *Curr. Microbiol.* 2015; 71:638-42, which is incorporated herein by reference in its entirety.

Further non-limiting targets of interest include 19-kDa protein (lipoprotein LpqH, 19 kDa lipoprotein antigen, putative transporter LpqH), e.g., from *M. tuberculosis, M. bovis,* or *M. avium,* or UniProt Entry No. P9WK61 (*M. tuberculosis,* strain ATCC 25618/H37Rv, Rv3763) or UniProt Entry No. A5U990 (*M. tuberculosis,* strain ATCC 25177/H37Ra) or UniProt entry No. A0A0H3M9Z0 (*M. bovis,* strain BCG/Pasteur 1173P2) or UniProt Entry No. P0A5J1 (*M. bovis,* strain ATCC BAA-935/AF2122/97); 38-kDa protein (phosphate-binding protein PstS 1, Pho S1, phoS, periplasmic phosphate-binding lipoprotein PstS 1 (PBP 1), 38 kDa lipoprotein, antigen Ag78, protein antigen B), e.g., from *M. tuberculosis* or *M. bovis* or UniProt Entry No. P9WGU1 (*M. tuberculosis,* strain ATCC 25618/H37Rv, Rv0934) or UniProt Entry No. A0A0H3M950 (*M. bovis,* strain BCG/Pasteur 1173P2); 40-kDa protein (alanine dehydrogenase, secreted L-alanine dehydrogenase, TB43, 40 kDa antigen), e.g., from *M. tuberculosis, M. avium* ssp. *paratuberculosis,* or *M. smegmatis,* or UniProt Entry No. P9WQB1 (*M. tuberculosis,* strain ATCC 25618/H37Rv, Rv2780) or UniProt Entry No. P9WQB0 (*M. tuberculosis,* strain CDC 1551/Oshkosh); Ag85 complex, including one or more Ag85A, Ag85B, and/or Ag85C proteins (e.g., any described herein); Ag85A protein (antigen 85A, diacylglycerol acyltransferase/mycolyltransferase Ag85A, acyl-CoA:diacylglycerol acyltransferase, Antigen 85 complex A, 85A, Ag85A, fibronectin-binding protein A, FbpA, Fbps A, mpt44 gene product), e.g., from *M. tuberculosis, M. bovis, M. leprae, M. avium, M. gordonae, M. ulcerans,* or *M. marinum,* or UniProt Entry No. P9WQP3 (*M. tuberculosis,* strain ATCC 25618/H37Rv, Rv3804c) or UniProt Entry No. P9WQP2 (*M. tuberculosis,* strain CDC 1551/Oshkosh) or UniProt Entry No. A1KQD8 (*M. bovis,* strain BCG/Pasteur 1173P2) or UniProt Entry No. P0C2T1 (*M. bovis,* strain ATCC BAA-935/AF2122/97); Ag85B protein (antigen 85B, diacylglycerol acyltransferase/mycolyltransferase Ag85B, DGAT, 30 kDa extracellular protein, acyl-CoA:diacylglycerol acyltransferase, Antigen 85 complex B, 85B, Ag85B, extracellular alpha-antigen, fibronectin-binding protein B, FbpB, Fbps B), e.g., from *M. tuberculosis, M. bovis, M. intracellulare, M. leprae, M. kansasii, M. avium, M. smegmatis,* or *M. africanum,* or UniProt Entry No. P9WQP1 (*M. tuberculosis,* strain ATCC 25618/H37Rv, Rv1886c) or UniProt Entry No. A5U3Q3 (*M. tuberculosis,* strain ATCC 25177/H37Ra) or UniProt Entry No. P9WQP0 (*M. tuberculosis,* strain CDC 1551/Oshkosh) or UniProt Entry No. P0C2T2 (*M. bovis,* strain ATCC BAA-935/AF2122/97); Ag85C protein (antigen 85C, diacylglycerol acyltransferase/mycolyltransferase Ag85C, DGAT, acyl-CoA:diacylglycerol acyltransferase, Antigen 85 complex C, 85C, Ag85C, fibronectin-binding protein C, FbpC, Fbps C, mpt45 gene product), e.g., from *M. tuberculosis, M. bovis, M. leprae, M. caprae, M. avium,* or *M. africanum,* or UniProt Entry No. P9WQN9 (*M. tuberculosis,* strain ATCC 25618/H37Rv) or UniProt Entry No. P9WQN8 (*M. tuberculosis,* strain CDC 1551/Oshkosh) or UniProt Entry No. P0A4V5 (*M. bovis,* strain ATCC BAA-935/AF2122/97); catalase peroxidase (KatG, CP, peroxidase/catalase, catalase-peroxidase-peroxynitritase T, KatG protein), e.g., from *M. tuberculosis* or *M. bovis,* or UniProt Entry No. P9WIE5 (*M. tuberculosis,* strain ATCC 25618/H37Rv, Rv1908c) or UniProt Entry No. P46817 (*M. bovis,* strain ATCC BAA-935/AF2122/97) or UniProt Entry No. A5U3S7 (*M. tuberculosis,* strain ATCC 25177/H37Ra) or UniProt Entry No. P9WIE4 (*M. tuberculosis,* strain CDC 1551/Oshkosh) or UniProt Entry No. H8F3Q9 (*M. tuberculosis,* strain ATCC 35801/TMC 107/Erdman); cord factor (trehalose 6,6'-dimycolate, TDM); cytochrome D ubiquinol oxidase (CydA, cytochrome BD ubiquinol oxidase subunit I, cytochrome BD-I oxidase subunit I, probable integral membrane cytochrome D ubiquinol oxidase (subunit I), AppC protein), e.g., from *M. tuberculosis, M. bovis, M. africanum, M. canetti, M. marinum,* or *M. microti,* or UniProt Entry No. L7N662 (*M. tuberculosis,* strain ATCC 25618/H37Rv, Rv1623c) or UniProt Entry No. Q7D892 (*M. tuberculosis,* strain CDC 1551/Oshkosh) or UniProt Entry No. A0A0H3P3B4 (*M. bovis,* ATCC BAA-935/AF2122/97); 2,3-diacyltrehalose (DAT or SL IV antigen); ES-6 (excretory-secretory protein 6-kDa antigen), e.g., from *M. tuberculosis*; serine protease ES-31 (ESAS-7F, 31-kDa antigen, SEVA TB ES-31 protein antigen); ES-43 (excretory-secretory 43-kDa antigen), e.g., from *M. tuberculosis* H37Ra; ESAT-6 (6 kDa early secretory antigenic target, EsxA), e.g., from *M. tuberculosis, M. bovis, M. africanum, M. kansasii, M. leprae,* or *M. marinum,* or UniProt Entry No. P9WNK7 (*M. tuberculosis,* strain ATCC 25618/H37Rv, Rv3875) or UniProt Entry No. P9WNK6 (*M. tuberculosis,* strain CDC 1551/Oshkosh) or UniProt Entry No. P0A565 (*M. bovis,* strain ATCC BAA-935/AF2122/97) and/or recombinant forms or fusion products thereof (e.g., the recombinant ESAT-6/CFP-10 heterodimer); ESAT-6-like proteins, such as ESAT-6-like protein EsxB (10 kDa culture filtrate antigen CFP-10, secreted antigenic protein MTSA-10, CFP10 protein, MTSA10 protein), e.g., from *M. tuberculosis* or *M. bovis,* or UniProt Entry No. P9WNK5 (*M. tuberculosis,* strain ATCC 25618/H37Rv, Rv3874) or UniProt Entry No. P9WNK4 (*M. tuberculosis,* strain CDC 1551/Oshkosh) or UniProt Entry No. P0A567 (*M. bovis,* strain ATCC BAA-935/AF2122/97) and/or recombinant forms thereof (e.g., the recombinant ESAT-6/CFP-10 heterodimer); ESX-1 secretion-associated protein EspB (EspB protein, antigen MTB48, Mtb48 protein), e.g., from *M. tuberculosis* or UniProt Entry No. P9WJD9 (*M. tuberculosis,* strain ATCC 25618/H37Rv, Rv3881c); ESX-1 secretion-associated protein EspC (EspC protein, Snm9 protein, ESX-1 secreted virulence factor), e.g., from *M. tuberculosis* or UniProt Entry No. P9WJD7 (*M. tuberculosis,* strain ATCC 25618/H37Rv, Rv3615c); heat shock protein HspX (alpha-crystallin, alpha-crystallin homolog, 14 kDa antigen, 16 kDa, HSP16.3, Nox16), e.g., from *M. tuberculosis, M. bovis, M. marinum,* or *M. smegmatis,* or UniProt Entry No. P9WMK1 (*M. tuberculosis,* strain ATCC 25618/H37Rv, Rv2031c) or UniProt Entry No. P9WMK0 (*M. tuberculosis,* strain CDC 1551/Oshkosh) or UniProt Entry No. P0A5B8 (*M. bovis,* strain ATCC BAA-935/AF2122/97) and/or recombinant forms or fusion products thereof (e.g., a Ag85B-Hsp16.3 fusion protein); hypoxic response protein 1 (Hrp1), e.g., from *M. tuberculosis* or *M. bovis,* or UniProt Entry No. P9WJA3 (*M. tuberculosis,* strain ATCC 25618/H37Rv, Rv2626c) or UniProt Entry No. P9WJA2 (*M. tuberculosis,* strain CDC 1551/Oshkosh) or UniProt Entry No. A0A0H3P8L8 (*M. bovis,* strain ATCC BAA-935/AF2122/97); possible Inv protein, e.g., from *M. tuberculosis* or *M. bovis,* or UniProt Entry No. 006624 (*M. tuberculosis,* strain ATCC 25618/H37Rv, Rv1566c) or UniProt Entry No. A0A0H3P3H0 (*M. bovis,* strain ATCC BAA-935/AF2122/97) or UniProt Entry No. A0A0H3M488 (*M. bovis,* (strain BCG/Pasteur 1173P2); Kp-90 immuno-cross-reactive antigenic compound (ImCRAC, Kp90 antigen), e.g., as described in U.S. Pat. No. 6,733,983 or available from Kreatech Diagnostics, Madrid, Spain, which is incorporated herein by reference in its entirety; lipoarabinomannan (LAM); lipoarabinomannan carrier protein LprG (lipoprotein LprG, 27 kDa lipoprotein, antigen P27, P27 protein, triacylated glycolipid carrier LprG), e.g., from *M. tubercu-* losis, M. bovis, or M. leprae, or UniProt Entry No. P9WK45 (M. tuberculosis, strain ATCC 25618/H37Rv, Rv1411c) or UniProt Entry No. A5U2B3 (M. tuberculosis, strain ATCC 25177/H37Ra) or UniProt Entry No. P9WK44 (M. tuberculosis, strain CDC 1551/Oshkosh) or UniProt Entry No. P0A5I9 (M. bovis, strain ATCC BAA-935/AF2122/97); malate synthase (malate synthase G, GlcB protein), e.g., from M. tuberculosis, M. bovis, or M. marinum, or UniProt Entry No. P9WK17 (M. tuberculosis, strain ATCC 25618/H37Rv, Rv1837c) or UniProt Entry No. P9WK16 (M. tuberculosis, strain CDC 1551/Oshkosh) or UniProt Entry No. A5U3K4 (M. tuberculosis, strain ATCC 25177/H37Ra) or UniProt Entry No. P0A5J5 (M. bovis, strain ATCC BAA-935/AF2122/97); methylmalonate-semialdehyde dehydrogenase (MmsA, methylmalonic acid semialdehyde dehydrogenase, MMSDH), e.g., from M. tuberculosis, M. bovis, M. africanum, M. canetti, or M. marinum, or UniProt Entry No. O53816 (M. tuberculosis, strain ATCC 25618/H37Rv, Rv0753c); cell surface lipoprotein MPB83 (lipoprotein p23), e.g., that binds to antibody MBS43, UniProt Entry No. P0CAX7 (M. bovis, strain ATCC BAA-935/AF2122/97), or UniProt Entry No. C1AFY9 (M. bovis, strain BCG/Tokyo 172/ATCC 35737/TMC 1019); immunogenic protein MPB70, e.g., that binds to antibody 1-5C; or UniProt Entry No. P0A669 (M. bovis, strain ATCC BAA-935/AF2122/97); immunogenic protein MPT32 (alanine and proline-rich secreted protein, Apa protein, DPEP, 45 kDa glycoprotein, 45/47 kDa antigen, antigen MPT-32, FAP-B, fibronectin attachment protein), e.g., from M. tuberculosis or M. canetti, or UniProt Entry No. P9WIR6 (M. tuberculosis, strain CDC 1551/Oshkosh) or UniProt Entry No. P9WIR7 (M. tuberculosis, strain ATCC 25618/H37Rv, Rv1860); MPT51 (MPT51/MPB51 antigen, MPT51/MPB51 antigen 85 complex C, AG58C, mycolyl transferase 85C, fibronectin-binding protein C, 85C, FbpC1, FbpD, MPB51), e.g., from M. tuberculosis, M. bovis, M. avium, M. smegmatis, M. africanum, or M. canetti, or UniProt Entry No. P9WQN7 (M. tuberculosis, strain ATCC 25618/H37Rv, Rv3803c) or UniProt Entry No. P0A4V7 (M. bovis, strain ATCC BAA-935/AF2122/97); immunogenic protein MPT63 (16 kDa immunoprotective extracellular protein, antigen MPT63, antigen Mpt63/MPB63), e.g., from M. tuberculosis, M. bovis, M. avium, M. africanum, or M. canetti, or UniProt Entry No. P9WIP1 (M. tuberculosis, strain ATCC 25618/H37Rv, Rv1926c); immunogenic protein MPT64 (antigen MPT64, antigen Mpt64/MPB64, MPB64), e.g., from M. tuberculosis, M. bovis, M. avium, M. marinum, or M. canetti, or UniProt Entry No. P9WIN9 (M. tuberculosis, strain ATCC 25618/H37Rv, Rv1980c); acyltransferase PapA3 (polyketide synthase-associated protein A3), e.g., from M. tuberculosis, or UniProt Entry No. P9WIK5 (M. tuberculosis, strain ATCC 25618/H37Rv, Rv1182) or UniProt Entry No. P9WIK4 (M. tuberculosis, strain CDC 1551/Oshkosh); peptidyl-prolyl cis-trans isomerase A PpiA (Cfp22 protein, iron-regulated peptidyl-prolyl cis-trans isomerase A, rotamase A, PPlase A, cyclophilin), e.g., from M. tuberculosis, M. bovis, M. africanum, M. marinum, or M. canetti, or UniProt Entry No. P9WHW3 (M. tuberculosis, strain ATCC 25618/H37Rv, Rv0009) or UniProt Entry No. P65763 (M. bovis, strain ATCC BAA-935/AF2122/97); proline-rich 28 kDa antigen (secreted proline rich protein Mtc28, MTC28), e.g., from M. tuberculosis, M. bovis, M. africanum, M. marinum, or M. canetti, or UniProt Entry No. P9WIM9 (M. tuberculosis, strain ATCC 25618/H37Rv, Rv0040c) or UniProt Entry No. P0A5Q7 (M. bovis, strain ATCC BAA-935/AF2122/97); triglycosyl-phenol phtiocerol dimycocerosate (PGLTb1, PGL-Tb1, triglycosyl phenolic glycolipid); thioredoxin (Trxc, TrxA, Trx, MPT46), e.g., from M. tuberculosis, M. bovis, M. africanum, M. marinum, or M. canetti, or UniProt Entry No. P9WG67 (M. tuberculosis, strain ATCC 25618/H37Rv, Rv3914) or UniProt Entry No. A5U9P2 (M. tuberculosis, strain ATCC 25177/H37Ra) or UniProt Entry No. P0A617 (M. bovis, strain ATCC BAA-935/AF2122/97); tuberculophosphatide (A3 antigen); anti-tuberculous glycolipid immunoglobulin G (anti-TBGL) antibody; resuscitation-promoting factor RpfB, e.g., from M. tuberculosis, M. bovis, or M. smegamatis, or UniProt Entry No. P9WG29 (M. tuberculosis, strain ATCC 25618/H37Rv, Rv1009); protein Rv2204c, e.g., from M. tuberculosis or M. bovis or UniProt Entry No. P9WMN5 (M. tuberculosis, strain ATCC 25618/H37Rv, Rv2204c); nucleoid-associated protein Rv3716c, UniProt Entry No. P9WNR9 (M. tuberculosis, strain ATCC 25618/H37Rv, Rv3716c), as well as a corresponding antigen/antibody thereof, a corresponding gene thereof, a gene product thereof, a fusion product thereof, a fragment thereof, a recombinant form thereof, a modified form thereof, a mutant thereof, and/or a complexed form thereof (e.g., for any target of interest described herein), in which any of these can be host-derived, non-host-derived, or synthesized in vivo or in vitro.

Multiplexed detection is also envisioned, in which a plurality of different targets is monitored to ensure adequate sensitivity and/or specificity of detection. Non-limiting exemplary multiplexed combinations of targets include the following: CFP-10), ESAT-6, and recombinant ESAT-6/CFP-10 heterodimer; 38-kDa, 16-kDa, ESAT-6, MPT63, 19-kDa, MPT64, MPT32, Rv1009, MTB48, Mtb81, MTC28, Ag85B, and KatG; ESAT-6, CFP-10, Ag85B, and Hsp16.3, optionally in combination with fusion protein Ag85B-Hsp16.3; 18-kDa, 40-kDa, 16-kDa, 31-kDa, 14-kDa, and 6-kDa; Hrp1 and Rv3615c; 38-kDa, Ag85A, MPT32, Rv2204c, MmsA, PpiA, Trxc, Rv2626c, KatG, and Rv3716c; PpiA, Ag85A, and MPT32; 38-kDa, LprG, Rv1566c, CydA, MPT64, and HspX; Mtb81, Mtb8, Mtb48, DPEP, and 38-kDa; or IgG, IgA, and IgM antibodies, LAM, and recombinant 38-kDa, as well as a corresponding antigen/antibody thereof, a corresponding gene thereof, a gene product thereof, a fusion product thereof, a fragment thereof, a recombinant form thereof, a modified form thereof, a mutant thereof, and/or a complexed form thereof (e.g., for any target of interest described herein), in which any of these can be host-derived, non-host-derived, or synthesized in vivo or in vitro.

Additional targets of interest are provided in, e.g., Pathakumari B et al., "Dynamic IgG antibody response to immunodominant antigens of M. tuberculosis for active TB diagnosis in high endemic setting," Clin. Chim. Acta 2016; 164:25-33; Zhang C et al., "Mycobacterium tuberculosis secreted proteins as potential biomarkers for the diagnosis of active tuberculosis and latent tuberculosis infection," J. Clin. Lab. Anal. 2015; 29:375-82; and Zhou F et al., "Protein array identification of protein markers for serodiagnosis of Mycobacterium tuberculosis infection," Sci. Rep. 2015; 5:15349 (10 pp.), each of which is incorporated herein by reference in its entirety, as well as a corresponding antigen/antibody thereof, a corresponding gene thereof, a gene product thereof, a fusion product thereof, a fragment thereof, a recombinant form thereof, a modified form thereof, a mutant thereof, and/or a complexed form thereof (e.g., for any target of interest described herein), in which any of these can be host-derived, non-host-derived, or synthesized in vivo or in vitro.

Further non-limiting targets of interest include cytokines and biomarkers (e.g., gene expression markers), e.g., APOC1, CD14, sCD40L, COMP, CPN2, G-CSF, IFN-γ, IGFBP6, IL-1Ra, IL-2, IL-5, IL-6, IL-7, IL-8, IL-9, IL-13, IL-15, IL-17, IP-10, LUM, MCP-1, PDGF, PEPD, PGLYRP2, PFN1, QSOX1, SELL, SEPP1, TAGLN2, TNF-α, TNXB, VASN, and/or VEGF-A; as well as Bcl2, BLR1, BPI, C14orf2, CASP8, CCL13, CCL19, CCL22, CCL4, CCR7, CD14, CD163, CD19, CD3c, CD4, CD8α, CTLA4, CXCL10, FASLG, FCGR1A, FOXP3, FPR1, IFN-γ, IL10, IL22RA1, IL2Ra, IL4, IL4d2, IL7R, LAG3, LTF, LY6G6D, MARCO, MMP9, NAT2, NCAM1, RAB13, RAB24, RAB33, RIN3, SEC 14L1, SPP1, TEX264, TGFB1, TGFBR2, TIMP2, TNF, TNFRSF18, TNFRSF1A, and/or TNFRSF1B, as well as any useful combinations thereof (e.g., G-CSF, IL-6, IL-7, IL-8, IL-9, and PDGF; IL-5, IL-9, IL-13, and IL-17; BPI, CCL19, FoxP3, FPR1, and TGFB1; Bcl2, BLR1, FCGR1A, IL4d2, and MARCO; etc.).

Centrifugal Devices

A microfluidic disc can be operated as a centrifugal device. In some instances, the device includes a substrate that may at least partially define an assay region, as well as a port (e.g., a sample port or inlet port) configured to receive a sample. The port can be in fluidic communication with any useful chamber (e.g., within an assay area) or any useful region of the device (e.g., an assay area). During operation, a sample (e.g., a fluid sample including a plurality of particles, such as beads or cells) may be transported by applying a centrifugal force that is directed from an interior of the microfluidic disc toward a periphery of the microfluidic disc. The centrifugal force may be generated by rotating the microfluidic disc in any useful direction.

The device can be designed to facilitate multiplexed detection, in which multiple samples can be processed at the same time and/or each particular sample can be divided to be tested for multiple different targets. For instance, the device can include a plurality of assay areas configured for multiplexed and/or parallel detection.

Assay Areas, Including Detection Regions

An assay area includes any portion defined in part by a substrate, in which the assay area facilitates one or more reaction(s), separation(s), and/or detection of a desired target. The assay area can be defined by one or more chambers (e.g., a reagent chamber, an assay chamber, an incubation chamber, as well as channels connecting any useful chamber) in fluidic communication with a sample port configured to receive a test sample. The assay area can include a detection region, which can be a chamber (e.g., a channel) configured to allow for detection of a signal emitted by a label agent that can optionally be affixed directly or indirectly to the target and/or a particle (e.g., a bead or a cell).

During operation, a centrifugal force may generally be used to transport a fluid sample (optionally including particles) from an inlet port (e.g., a sample port) toward an assay area (e.g., a detection region of the assay region). Additionally, centrifugal forces may be used to transport density medium and/or particles from one or more reservoir(s) to the assay area.

The density medium can have a density greater than that of the fluid sample but lower than that of the particles to be detected. These differences in density can be employed to separate the particles from the fluid sample. By applying centrifugal force, flows are induced. Denser particles from the fluid sample are transported through the density medium, but the less dense components of the fluid sample are not transported through the density medium. In this manner, the particles (e.g., bound to one or more targets) are selectively separated from the remaining portions of the test sample, and detection limits can display improved sensitivity and/or selectivity.

The assay area can include a narrowed or tapered region, which can facilitate detection within the assay area. For instance, upon providing a centrifugal force, a sedimentation-based assay can be conducted within the assay area, such that a pellet is formed in a portion of the assay area closest to the edge of the microfluidic device. If this portion terminates in a narrowed or tapered region, then the pellet is distributed across a larger surface area, which may be more effective at transmitting a detection signal. In one instance, a fluorescence signal can be more easily detected across this narrowed region due to reduced scattering, thereby increasing the sensitivity of the assay. Accordingly, the assay area can have any useful dimension (e.g., width, height, radius, depth, etc.) and/or cross-section (e.g., rectangular, triangular, semi-circular, rounded, trapezoidal, etc.) that can be uniform or non-uniform along any axis or dimension. Further details on narrowed or tapered regions are described in U.S. Pat. No. 8,962,346, which is incorporated herein by reference in its entirety.

Chambers

The present apparatus (e.g., device, such as a microfluidic disc) can include one or more chambers, which can be configured to substantially enclose a fluid or a substance in the fluidic device (e.g., a microfluidic disc). Such chambers can include one or more ports (e.g., inlets or outlets), fluidic opening (e.g., vias), fluidic barriers, channels, or any other structure to allow for fluidic communication between one or more chambers, vents, etc. Exemplary chambers include a channel, a reservoir, etc., having any useful geometry or dimension.

The chambers can be designated for a particular use. Particular uses for such chambers include a sample chamber for receiving and/or storing a test sample, an incubation chamber for incubating a test sample, a reaction chamber for reacting a test sample or a processed sample with another agent or reagent, a reagent chamber containing one or more reagents or agents for detecting one or more targets (e.g., containing one or more label agents), a sterilization chamber containing one or more reagents or agents to sterilize or disinfect the test sample (e.g., containing one or more sterilization agents, as described herein), an assay chamber for conducting one or more assays to detect one or more targets, a post-processing chamber to perform one or more procedures (e.g., lysis, polymerase chain reaction (PCR), amplification assay, immunoassay, analytic test, and/or biochemical analysis), and/or a waste chamber for storing one or more by-products of the assay. Each of these chambers can be interconnected by a valve (e.g., a passive valve, an active valve, an NC valve, and/or NO valve) and/or a channel that can optionally include such a valve in its fluidic path.

Substances and materials within a chamber can be transported to any other chamber in any useful manner. In one instance, rotation over a certain threshold results in transporting a reagent or agent from a first chamber to another chamber (e.g., from a reservoir to a chamber in the assay area; or from a sample port to a reservoir; or from a sample port to a chamber in the assay area). In other instances, a channel can have a dimension that requires a certain rotation rate to overcome capillary pressure, such that the channel functions as a valve. In other instances, the channel includes a wax-based valve that requires melting for actuation. Other methods of controlling flow in microfluidic devices (e.g., pressure-induced flow, centrifugal force-driven flow, pumping, etc.) are known and can be implemented with the devices and systems herein.

Microfluidic Devices and Systems

An exemplary system can include one or more modules or components to facilitate performing assays with the microfluidic disc. In one non-limiting instance, the system includes a microfluidic disc, a motor module coupled to the disc and configured to spin the disc in order to generate centrifugal forces, a detection module positioned to detect a signal from one or more label agents in the assay area (e.g., within a detection region), and an optional processing device. An optional actuator may be coupled to the detection module and configured to move the detection module along the detection region in some examples.

In one instance, the motor module may be implemented using a centrifugation and/or stepper motor. The motor module may be positioned relative to the detection module, such that placing the disc on the motor ensures that an assay area, or a portion thereof, is exposed to the detection module. The motor module can include any useful motor, e.g., a brushed DC motor, a solenoid, a servo motor, a linear actuator, as well as combinations thereof.

The detection module may include a detector (e.g., an electronic detector, an optical detector, a cell phone camera, a photodiode, a photomultiplier tube, and/or a CCD camera) suitable for detecting a signal from one or more label agents (e.g., affixed to particles to be detected and/or quantified). The detector module may include, for example, a laser and optics suitable for optical detection of fluorescence from fluorescent labels. In other examples, other detectors, such as electronic detectors, may be used. An optional actuator may move the detector to a variety of locations of the microfluidic disc (e.g., along the assay area) to detect a measurable signal. The one or more actuators may be coupled to the motor module and/or disc, such that the disc is moved relative to the detection module in response to signals from the processing device.

A processing device may be coupled to the motor module, the detection module, and/or the actuator. Furthermore, the processing device can be configured to provide one or more signals (e.g., one or more control signals to those modules and/or components), as well as to receive one or more signals (e.g., one or more electronic signals from the detection module corresponding to the presence or absence of label agent). All or selected components or modules may be housed in a common housing or in separate enclosures (e.g., optionally configured to operate together, such as by providing a hinged housing formed by connecting an upper enclosure to a lower enclosure by use of a hinge). Microfluidic discs may be placed on the motor module and removed, such that multiple discs may be analyzed by the system.

The processing device may include one or more processing units, such as one or more processors. In some examples, the processing device may include a controller, logic circuitry, and/or software for performing functionalities described herein. The processing device may be coupled to one or more memories, input devices, and/or output devices including, but not limited to, disc drives, keyboards, mice, and displays. The processing device may provide control signals to the motor module to rotate the microfluidic disc at selected speeds for selected times. The processing device may provide control signals to the detection module (e.g., including one or more detectors and/or actuators), detect signals from the label agent(s), and/or move the detector to particular locations. The processing device may develop these control signals in accordance with input from an operator and/or in accordance with software. The software may include one or more executable instructions (e.g., stored on one or more memories) configured to cause the processing device to output a predetermined sequence of control signals, to perform one or more calculations (e.g., determine the presence or absence of a target based on electronic signals from the detection module), to communicate any useful output (e.g., a result, a setpoint, a level, etc.) over a network, to store any useful output in memory, and/or display any useful output on a display module. It is to be understood that the configuration of the processing device and related components is quite flexible, and any of a variety of computing systems may be used including server systems, desktops, laptops, controllers, and the like.

The system can include any other modifications to facilitate rotation of the device and/or detection within the device. In one instance, the device includes a structure configured to align an assay area with a detection module. In one non-limiting embodiment, an assay area can include a corresponding tooth element. In another non-limiting embodiment, each assay area includes a corresponding tooth element. In yet another non-limiting embodiment, one tooth element can be an extended tooth element having a different dimension than another tooth element. In use, the system can include a device including a plurality of assay regions and corresponding tooth elements; a motor module configured to move the device such that the assay areas move along a first path (e.g., a circular path disposed on a surface of the device) and the tooth elements move along a second path (e.g., a circular path disposed on an edge or along a periphery of the device); an impinging element configured for placement in a first position that allows for movement of device and a second position, wherein the impinging element engages at least one tooth element when in the second position; a detection module configured to detect a signal (e.g., arising the detection region or the assay area; arising from one or more label agents or one or more targets); and processing device (e.g., a controller) communicatively coupled to the impinging element and the motor module, where the processing device is configured to provide a control signal to the impinging element to place the impinging element in the first position or the second position. In some embodiments, the detection module is positioned such that when the impinging element is in the second position, the detection module is aligned with at least one of the plurality of assay regions.

Exemplary devices (e.g., apparatuses) and systems, as well as methods employing such devices and systems, are described in U.S. Pat. Nos. 8,945,914 and 9,186,668, as well as U.S. Pat. Appl. Pub. No. 2015/0360225, each of which is incorporated herein by reference in its entirety.

Density Medium and Particles

The present invention can be employed with any useful agents, including a density medium, a particle, as well as combinations thereof. The density medium may have a density lower than a density of a plurality of particles (e.g., beads or cells) and higher than a density of the fluid sample. The density medium may generally be implemented using a fluid having a density selected to be in the appropriate range, e.g., lower than a density of the particles to be detected or quantified and higher than a density of the fluid sample. In some examples, a fluid sample may be diluted for use with a particular density medium. The density medium may include, for example, a salt solution containing a suspension of silica particles, which may be coated with a biocompatible coating (e.g., a polyvinylpyrrolidone (PVP) coating or a silane coating). In some embodiments, the density medium is a dense solution (e.g., a solution denser than water, including an aqueous solution having a polymer, a sugar, a carbohydrate, an ionic salt, a saccharide, an alcohol, a polyhydric alcohol, as well as polymeric forms thereof, conjugated forms thereof, iodinated forms thereof, or modified forms thereof). In other embodiments, the density medium is an ionic gradient media (e.g., a solution including one or more inorganic salts and/or heavy metal salts, such as cesium chloride, cesium sulfate, lithium chloride, potassium bromide, sodium polytungstate, etc.). In yet other embodiments, the density medium is an iodinated gradient media (e.g., a nonionic iodinated gradient media). In other embodiments, the density medium is a colloidal media, which is a colloidal suspension of one or more particles (e.g., coated particles).

Examples of suitable density media are PERCOLL™ (colloidal silica coated with PVP), PERCOLL™ PLUS (colloidal silica coated with silane), FICOLL™ PM70 (high molecular weight sucrose-polymers with an average molecular weight of 70,000), FICOLL™ 400 (a copolymer of sucrose and epichlorohydrin), FICOLL™ PM400 (a synthetic neutral, highly-branched hydrophilic polymer of sucrose with an average molecular weight of 400,000), FICOLL-PAQUE™ PLUS (a combination of FICOLL™ PM400, sodium diatrizoate, and disodium calcium EDTA), and FICOLL-PAQUE™ Premium (a combination of FICOLL™ PM400, sodium diatrizoate, and disodium calcium EDTA in water for injection), each of which is available from GE Healthcare Life Sciences, Little Chalfont, Buckinghamshire, United Kingdom.

Other examples of suitable density media are HISTOPAQUE® (a combination of polysucrose and sodium diatrizoate, including a HISTOPAQUE®-1077 formulation adjusted to a density of 1.077 g/mL, a HISTOPAQUE®-1083 formulation adjusted to a density of 1.083 g/mL, and a HISTOPAQUE®-1119 formulation adjusted to a density of 1.119 g/mL), diatrizoate (e.g., meglumine diatrizoate or sodium diatriazoate), diatrizoic acid, diatrizoic acid dihydrate, iodixanol, iohexol (e.g., sold as HISTODENZ™ or NYCODENZ™), metrizamide, glycerol, sorbitol, sucrose (e.g., polysucrose), dextran, and dextran sulfate (e.g., dextran sulfate sodium salt), as well as salts of any of these, mixtures thereof, and solutions thereof.

Particular densities may be achieved by adjusting a percentage of the density medium in a salt solution. Generally, viscosity and density of the density medium may be adjusted by selecting a composition of the medium. Varying the concentration of solutes such as sucrose or dextran in the medium may adjust the density and/or viscosity.

In some instances, sedimentation assays can be conducted, in which the settling velocity of a particle is described by known Stoke's flow equations. Sedimentation rates typically scale with a square of a particle's radius and can be linearly dependent with the difference in density between a particle and a surrounding fluid (e.g., as provided by a sample or by a density medium). Thus, under certain conditions, a population of particles can be separated according to its density and/or radius.

Particles of different sizes can be employed, in which the different sedimentation rates can be used to allow size-based separation and/or detection. The sedimentation rate of a particle is dependent on various characteristics of the particle, including particle size (e.g., particle radius), particle surface charge, and/or particle density. Sedimentation can occur under any force, such as gravitational force or centrifugal force (e.g., by rotating or spinning a microfluidic device). In one non-limiting example, a first population of particles (e.g., having a first particle size and/or first particle density) can include a first type of capture agent, and a second population of particles (e.g., having a second particle size and/or second particle density) can include a second type of capture agent, thereby allowing for different sedimentation rates and/or separation zones for each population. For instance, smaller and/or less dense particles can be localized in a first separation zone, and larger and/or denser particles can be localized in a second separation zone, thereby allowing for separation of different populations of particles by employing centrifugal force. Further details on sedimentation assays are provided in U.S. Pat. No. 8,945,914, which is incorporated herein by reference in its entirety.

Particles can be composed of any useful material and have any useful chemical properties (e.g., surface charge, including a positively charged surface or a negatively charged surface). Exemplary materials include polystyrene, polymethylmethacrylate, silica, metal (e.g., gold, iron, or iron oxide), as well as combinations thereof and coated versions thereof (e.g., including a polymer coating, a charged coating, or a coating including binding groups, such reactive linkers, antibodies, integrins, and/or selectins). Particles can have any useful dimension (e.g., as in microparticles, nanoparticles, etc.) depending on their use. For example, particle dimensions may be useful for use as sedimentation particles, whereas other dimensions or characteristics for use as labeling particles. In one non-limiting instance, a sedimentation particle can be modified to bind to certain cells, thereby increasing the sedimentation rate of certain cells upon binding and allowing these certain cell types to be selectively removed from the sample during centrifugation.

Other substances, reagents, or agents can be employed in conjunction with the density medium and/or a population of particles. In one instance, a separation layer fluid is employed, which forms an interface between a density medium and a sample, between a sample and a particle, and/or between the density medium and the particle. This separation layer fluid can have nay useful density (e.g., denser than the density medium but less dense than the particle; denser than the sample but less dense than the density medium; or denser than the sample but less dense than the particle). The separation layer fluid can include any useful substance, e.g., a hydrophobic material, a mineral oil, an organic oil, a charged or water ordering polymer, a salt in a water-based medium, a fluoroalkane fluid, a perfluorocarbon, or a perfluoroalkane fluid. Further details on separation layer fluids are provided in U.S. Pat. Nos. 8,962,346 and 9,304,129, each of which is incorporated herein by reference in its entirety.

Dissociation Agents and Neutralization Agents

A dissociation agent includes any compound configured to dissociate an agent (e.g., a host-responsive protein, a host-derived protein, or a non-host-derived protein) from the target of interest. A neutralization agent, in turn, includes any compound configured to neutralize (e.g., the chemical effect) of the dissociation agent. For instance, if the non-limiting dissociation agent is an acid, then the neutralization agent can be a less acidic compound (e.g., a base). Similarly, if the non-limiting dissociation agent is a base, then the neutralization agent can be a less basic compound (e.g., an acid). Exemplary dissociation agents include an acid or an acidic buffer (e.g., HCl or HCl-glycine), and corresponding neutralization agents include a base or a more basic buffer (as compared to the dissociation agent, e.g., NaOH or $KH_2PO_4$).

Label Agents and Capture Agents

A label agent includes any moiety that can emit a signal suitable for detection, such as an optical or an electrical signal. The label agent can optionally include a capture portion, which binds to a target or a portion thereof. Furthermore, a label agent can be used in conjunction with a capture agent (e.g., as in a sandwich assay, which can include use of a capture agent to bind a first region of the target to a bead and use of a label agent to bind to a second region of the target in order to provide a detectable signal). Exemplary capture agents include a capture protein, a capture antibody, a capture antigen, or a capture nucleic acid.

Exemplary capture agents include a protein that binds to or detects one or more markers (e.g., an antibody or an enzyme), an affibody, an aptamer, a globulin protein (e.g., bovine serum albumin), a nanoparticle, a microparticle, a sandwich assay reagent, a nucleic acid (e.g., single stranded nucleic acid, double stranded nucleic acid, hairpin nucleic acid, DNA, RNA, cell-free nucleic acids, as well as chimeras thereof, hybrids thereof, or modifications thereof), a toxin capture agent (e.g., a sarcin-ricin loop capture agent), a major histocompatibility complex capture agent (e.g., a MHC II capture agent), or a catalyst (e.g., that reacts with one or more markers).

Exemplary label agents include a capture agent (e.g., any herein), a detectable molecule or compound (e.g., a probe (e.g., a fluorescence resonance energy transfer or FRET probe, a fluorescent probe, and/or a quencher probe), an electroactive label, an electrocatalytic label, a fluorescent label, a fluorogenic substrate (e.g., a non-fluorescent substrate capable of being activated to produce a detectable fluorescent signal), a chromogenic label, a chromogenic substrate (e.g., a non-chromogenic substrate capable of being activated to produce a detectable chromogenic signal), a colorimetric label, a quantum dot, a particle, a nanoparticle, a microparticle, a barcode, a radio label (e.g., an RF label or barcode), a magnetic label, a magnetic field sensor active label (e.g., a giant magneto resistive (GMR) sensor label or an anisotropic magnetoresistor (AMR) sensor label), a spin label, an electron resonance active label (e.g., an electron paramagnetic resonance (EPR) active label of an electron spin resonance (ESR) active label), avidin, biotin, a tag, a dye, a marker, an enzyme that can optionally include one or more linking agents and/or one or more dyes, etc.), or a combination of a capture agent with a detectable molecule or a detectable compound. Other exemplary label agents include nucleic acid dyes, lipid dyes, etc.

The capture agent can include any useful reactive group (e.g., a functional group that is one of a cross-linker group, a binding group, or a click-chemistry group, such as any described herein). Exemplary reactive groups include any chemical group configured to form a bond. In general, a first chemical group reacts with a second chemical group to form a bond (e.g., a covalent bond), in which the first and second chemical groups form a reactive pair.

In one instance, the reactive group is a cross-linker group. In another non-limiting instance, the reactive pair is a cross-linker reaction pair, which includes a first cross-linker group and a second cross-linker group that reacts with that first cross-linker group. Exemplary cross-linker groups and cross-linker reaction pairs include those for forming a covalent bond between a carboxyl group (e.g., —CO$_2$H) and an amino group (e.g., —NH$_2$); or between a phospho group (e.g., —P(O)(OH)$_2$) and an amino group (e.g., —NH$_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., —NH$_2$) and a thymine moiety, such as succinimidyl-[4-(psoralen-8-yloxy)]-butyrate (SPB); a hydroxyl group (e.g., —OH) and a sulfur-containing group (e.g., free thiol, —SH, sulfhydryl, cysteine moiety, or mercapto group), such as p-maleimidophenyl isocyanate (PMPI); between an amino group (e.g., —NH$_2$) and a sulfur-containing group (e.g., free thiol, —SH, sulfhydryl, cysteine moiety, or mercapto group), such as succinimidyl 4-(p-maleimidophenyl)butyrate (SMPB) and/or succinimidyl 4-(N-maleimidomethyl) cyclohexane-1-carboxylate (SMCC); between a sulfur-containing group (e.g., free thiol, —SH, sulfhydryl, cysteine moiety, or mercapto group) and a carbonyl group (e.g., an aldehyde group, such as for an oxidized glycoprotein carbohydrate), such as N-beta-maleimidopropionic acid hydrazide-trifluoroacetic acid salt (BMPH), 3-(2-pyridyldithio)propionyl hydrazide (PDPH), and/or a 3-(2-pyridyldithio)propionyl group (PDP); between a maleimide-containing group and a sulfur-containing group (e.g., free thiol, —SH, sulfhydryl, cysteine moiety, or mercapto group); between a sulfur-containing group (e.g., free thiol, —SH, sulfhydryl, cysteine moiety, or mercapto group) and an alkene group or an alkyne group; between a reactive carbene group (e.g., arising from photoactivation of a diazirine group) and a functional group having an active hydrogen group (e.g., as in an alkene group) and/or a nucleophilic group (e.g., as in a leaving group); and between a reactive nitrene group (e.g., arising from photoactivation of an aryl azide group) and a functional group having an active hydrogen group (e.g., as in an alkene group) and/or a nucleophilic group (e.g., as in a leaving group). Yet other cross-linkers include those for forming a covalent bond between two or more unsaturated hydrocarbon bonds, e.g., mediated by radical polymerization, such as a reaction of forming a covalent bond between a first alkene group and a second alkene group (e.g., a reaction between acrylate-derived monomers to form a polyacrylate, polyacrylamide, etc.). Other cross-linkers include those having photoactivatable groups, which upon photoreaction produces a reactive intermediate (e.g., such as cross-linkers including a benzophenone moiety, a diazirine moiety, or an aryl azide moiety).

In another instance, the reactive group is a binding group. In another non-limiting instance, the reactive pair is a binding reaction pair, which includes a first binding group and a second binding group that reacts with that first binding group. Exemplary binding groups and binding reaction pairs include those for forming a covalent bond between biotin and avidin, biotin and streptavidin, biotin and neutravidin, desthiobiotin and avidin (or a derivative thereof, such as streptavidin or neutravidin), hapten and an antibody, an antigen and an antibody, a primary antibody and a secondary antibody, lectin and a glycoprotein, and a nucleic acid and a complement thereof.

In yet another instance, the reactive group is a click-chemistry group. In another non-limiting instance, the reactive pair is a click-chemistry reaction pair, which includes a first click-chemistry group and a second click-chemistry group that reacts with that first click-chemistry group. Exemplary click-chemistry groups include, e.g., a click-chemistry group, e.g., one of a click-chemistry reaction pair selected from the group consisting of a Huisgen 1,3-dipolar cycloaddition reaction between an alkynyl group and an azido group to form a triazole-containing linker; a Diels-Alder reaction between a diene having a 4π electron system (e.g., an optionally substituted 1,3-unsaturated compound, such as optionally substituted 1,3-butadiene, 1-methoxy-3- trimethylsilyloxy-1,3-butadiene, cyclopentadiene, cyclohexadiene, or furan) and a dienophile or heterodienophile having a 2π electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group.

Other Reagents

The present device can be configured for use with any number of reagents either on-chip and/or off-chip. Exemplary reagents include a lysing agent (e.g., a detergent, such as saponin); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, a coated particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a buffer (e.g., a phosphate or borate buffer, which can optionally include one or more salts, kosmotropes, and/or chaotropes), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

Samples

The sample can include any useful targets. Exemplary targets include cells (e.g., white blood cells, red blood cells, neutrophils, lymphocytes, monocytes, granulocytes, tumor cells, etc.), viruses, viral proteins, bacteria, bacterial proteins, proteins, nucleic acids (or complements thereof), complexes, etc., as well as fragments, recombinant forms, or modified forms of any of these.

In some instances, the sample includes any useful test sample. The test sample can include any useful sample, such as a microorganism, a virus, a bacterium, a fungus, a parasite, a helminth, a protozoon, a cell (e.g., a cell culture), tissue (e.g., tissue homogenates), a fluid (e.g., a pleural fluid or an ascitic fluid), a swab, a biological sample (e.g., blood, such as whole blood, serum, plasma, saliva, urine, cerebral spine fluid, synovial fluid, etc. rom any subject, such as a human subject), a buffer, a plant, an animal, an agricultural sample, an environmental sample (e.g., air, soil, and/or water), etc. The sample can be optionally processed (e.g., on-chip or off-chip) in any useful manner (e.g., before or after transporting to the assay area, or even within the assay area), e.g., diluted, mixed, homogenized, lysed, sterilized, incubated, labeled, etc.

Diagnostic Methods

The microfluidic devices and systems herein can be adapted for any useful diagnostic technique. Exemplary diagnostic techniques include particle quantification (e.g., cell counting, differential white blood cell count), sedimentation assays, sandwich assay, nucleic acid assays, agglutination assays, toxin assays, amplification assays, etc.

In one instance, the devices and systems herein are adapted to detect one or more targets of interest in a sample. In one instance, the target can be correlated to an active infection (e.g., by a virus and/or a bacterium, such as any described herein). In particular non-limiting embodiments, the methods can discriminate between a sample from a subject having an active infection (by a target of interest) or a subject that has a latent infection (by a target of interest), thereby indicating past exposure to the target and not necessitating medical treatment. Exemplary bacterium includes a *mycobacterium*, such as *M. tuberculosis, M. marinum, M. kansasii*, and *M. bovis*; and exemplary bacterial infections include latent and active infections from a *mycobacterium* (e.g., any described herein).

In one non-limiting instance, the devices and systems herein are adapted to perform a method of conducting a sandwich assay. One exemplary method can include: providing a fluid sample in a channel on a microfluidic device (e.g., a microfluidic disc), the fluid sample including a plurality of particles (e.g., beads) having complexes formed thereon, individual ones of the complexes including a capture agent, a target (e.g., a target analyte), and a label agent, the fluid sample further including a free label agent; providing a density media from a media reservoir to an assay area (e.g., a detection region) of the microfluidic device by applying a first centrifugal force, the media reservoir on the microfluidic disc and in fluid communication with the assay area, the assay area fluidly coupled to the channel, where the density media has a density within a range, an upper bound of the range being lower than a density of the plurality of particles and a lower bound of the range being higher than a density of the fluid sample; transporting the plurality of particles including the complexes through the density media, where the free label agent is restricted from transport through the density media, and where a first plurality of particles having a first property is transported to a first distinct detection location in the assay area and a second plurality of beads having a second property different than the first property is transported to a second distinct detection location in the assay area; detecting a signal from the label agents of the complexes; and generating an electronic detection signal based, at least in part, on the signal detected from the label agents. The method can optionally include, prior to the transporting step, spinning the microfluidic device to apply a second centrifugal force on the plurality of particles, the first and second centrifugal forces being different.

In another non-limiting instance, the devices and systems herein are adapted to perform a method of conducting an assay (e.g., a sedimentation assay). An exemplary method can include: layering a mixture on a density medium in an assay area, where the mixture includes a sample, a first separation layer fluid, and a plurality of sedimentation particles, where the sedimentation particles have a density greater than the density medium, and where the layering a mixture includes forming, with the first separation layer fluid, an interface between the density medium and the sample, between the sample and the sedimentation particles, or between the density medium and the sedimentation particles; subjecting the mixture to a sedimentation force such that the sedimentation particles, if formed, travel through the first separation layer fluid and the density medium to a detection area; and detecting a presence of an analyte of interest in the detection area. Other exemplary assays (e.g., sandwich assays and sedimentation assays) are described in U.S. Pat. Nos. 8,945,914 and 8,962,346, each of which is incorporated herein by reference in its entirety.

In yet another non-limiting instance, the devices and systems herein are adapted to perform a method of conducting an agglutination assay. An exemplary method can include: layering a mixture on a density medium, where the mixture includes a sample and a first population of coated particles (e.g., coated beads) having a first density, where the first population includes a capture agent (e.g., an affinity reagent) for a target (e.g., an analyte of interest), where the first population is configured to form aggregates with the target when present, where the density medium has a minimum density greater than the first density; subjecting the mixture to a sedimentation force such that the aggregates, if formed, travel through the density medium; and detecting a presence of the aggregates in an assay area (e.g., a detection area or a detection region). Other exemplary agglutination assays are described in U.S. Pat. No. 9,244,065, which is incorporated herein by reference in its entirety.

In another non-limiting instance, the devices and systems herein are adapted to perform a method of conducting a toxin activity assay. An exemplary method can include: generating a plurality of complexes on a plurality of particles (e.g., beads) by action of an active toxin in a fluid sample, individual complexes of the plurality of complexes including a capture agent and a label agent; transporting the plurality of particles including the complexes through a density medium, where the density medium has a density lower than a density of the particles and higher than a density of the fluid sample, and where the transporting occurs, at least in part, by sedimentation; and detecting a signal from the label agents of the plurality of complexes bound to the plurality of particles. Other exemplary toxin activity assays are described in U.S. Pat. No. 9,304,128, which is incorporated herein by reference in its entirety.

In yet another non-limiting instance, the devices and systems herein are adapted to perform a method of conducting a metabolite test. An exemplary system can include: a chamber that includes a fluid, and is configured to accept a sample fluid, where the sample fluid includes a delta-9-THC compound and a metabolite (e.g., a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound); and a detection module that, responsive to a centrifugal force being applied to the fluid and the sample fluid, outputs an indication of a level of the delta-9-THC compound and/or the metabolite in the sample fluid.

An exemplary method can include: exposing an agent (e.g., a capture agent, a label agent, or a combination thereof, such as a fluorophore-labelled analyte specific antibody) to a first fluid including at least one of: a free analyte, where the free analyte, if present in the first fluid, originates from a test sample added to the first fluid; or a bound analyte, where the bound analyte, if present in the first fluid, is attached to a first particle having a first density, the agent has a stronger binding affinity for the free analyte than for the bound analyte, the first fluid is in a chamber, the chamber has an open end and a closed end and further includes a second liquid, the second liquid is located at the closed end of the chamber and the first liquid is located between the second liquid and the open end of the chamber; applying a centrifugal force to the chamber, wherein the first particle transfers from the first liquid to the second liquid; irradiating the second liquid to generate a detectable signal in the second liquid (e.g., with light energy to generate fluorescence in the second liquid); and quantifying an amount of free analyte in the second liquid based upon a magnitude of the detectable signal at the second liquid, where the quantification is based upon a threshold value. In some embodiments, the second liquid includes a colloidal suspension of silicon nanoparticles, dextran, poly(ethylene glycol), glycerol, sorbitol, iodixanol, cesium chloride, or perfluorodecalin.

Materials

The present devices and systems can be formed from any useful material. Exemplary materials include a polymer, such as polymethyl methacrylate (PMMA), polyethylene terephthalate (PET, e.g., biaxially-oriented PET or bo-PET), an acrylic polymer, poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof; silicon; glass; quartz; fused silica; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organotin compounds), antioxidants (e.g., phenols or amines), and/or UV stabilizers (e.g., benzophenones or salicylates). Such materials can be provided in any useful form, such as in one or more layers that can be laminated to provide the assembled cartridge; and fabricated in any useful manner, such as by way of embossing, etching, injection molding, surface treatments, photolithography, bonding and other techniques.

EXAMPLES

Example 1: Simultaneous Detection of Proteins for Co-Infected Patients

Co-infections can be challenging to diagnose and treat. For instance, a patient may exhibit clinical symptoms that may not be specific to any one of the co-infections. In addition, laboratory tests can have markedly different sensitivity and specificity for the same biomarker present in a co-infected individual. For example, the presence of a particular biomarker can indicate an infection by a single infective agent, but testing for that particular biomarker may provide a false-negative result in a co-infected patient.

Infection with *Mycobacterium tuberculosis* (*M. tuberculosis*) represents a significant threat to people with immune disorders, such as HIV-positive individuals. Co-infection with HIV and tuberculosis can result in significant health complications or death, if not diagnosed and treated early. For instance, when diagnosing tuberculosis (TB) by using an IFN-γ assay for HIV patients, the assay might produce a false-negative result due to low production of IFN-γ in HIV-positive patients. The sights of *mycobacterium* infection (e.g., CD4 and T-cells) are also ideal sites for HIV replication. The increase of viral load on the immune system and macrophages, co-infected with both HIV and *M. tuberculosis*, can result in an acute TB infection due to the prior HIV infection.

Herein, we describe devices, systems, and methods for enhanced detection of a target of interest. In particular, such detection can include multiplexed detection of various analytes that can directly indicate, e.g., active infection by a non-host pathogen, such as a bacterium or a virus. Accordingly, in one non-limiting embodiments, described herein is a centrifugal microfluidic platform for multiplexed detection of tuberculosis and HIV biomarkers in human whole blood with minimal sample preparation and a sample-to-answer time of about 30 minutes. This multiplexed assay was developed for the detection of two *M. tuberculosis* secreted proteins, whose secretion represents an active and ongoing infection, as well as detection of HIV p24 protein and human anti-p24 antibodies. The limit of detection for this multiplex assay is in the pg/mL range for both HIV and *M. tuberculosis* proteins, making this assay potentially useful in the clinical diagnosis of both HIV and tuberculosis proteins indicative of active infection. Additional details are provided herein.

Example 2: Experimental Methods

This Example provides exemplary materials and methods useful for any methods, devices, and systems herein.

Detection of targets of interest include non-host proteins (e.g., bacterial proteins derived from *M. tuberculosis* or viral proteins derived from HIV), as well as host-responsive proteins (e.g., human anti-HIV p24 antibody). Capture agents can include any protein that can bind to the target of interest, in which exemplary capture agents include antibodies that can bind a non-host protein or a protein that can bind a host-responsive antibody. Proteins and antibodies can include the following: *M. tuberculosis* Ag85B full-length protein (Product code ab83471), rabbit polyclonal anti-Ag85B antibody (Product code ab43019), and recombinant *M. tuberculosis* 38-kDa full length protein (Product code ab119461) were purchased from Abcam (Abcam plc, Cambridge, UK; Cambridge, Mass.). Anti-38-kDa protein monoclonal antibodies (Cat. No. NB 100-73190, Clone HTM81 and Cat. No. NB 100-73191, Clone HTM82) were purchased from Novus Biologicals, LLC (Littleton, Colo.). Anti-HIV1 p24 antibodies (Product codes ab9071 and ab9072) were purchased from Abcam. Human polyclonal anti-p24 antibody (Item No. 2503, IgG fraction purified from HIV-1 immune human serum) and recombinant HIV gag p24 protein (Item No. 1003, produced in the baculovirus expression system) were purchased from ImmunoDX, LLC (Woburn, Mass.). Mouse anti-human IgG antibody (FC-AF488) was purchased from SouthernBiotech (Southern Biotechnology Associates, Inc., Birmingham, Ala.).

Any useful particle (e.g., bead or microsphere) can be employed to be functionalized with any capture agent described herein. Particles can include microspheres, e.g., ALEXA FLUOR® 488 (fluorescent dye) Fluorescent Microspheres (Cat. No. T8864, TRANSFLUOSPHERES® carboxylate-modified microspheres, 0.04 m) and ALEXA FLUOR® 647 (fluorescent dye) Fluorescent Microspheres (Cat. No. A20186) obtained from INVITROGEN™ (Waltham, Mass.; brand for Thermo Fisher Scientific Inc., Eugene, Oreg.); as well as carboxylic acid functionalized silica microspheres (Cat. Code SC06N/11491) obtained from Bangs Laboratories, Inc. (Fishers, Ind.).

Other exemplary reagents include the following: a wash buffer, such as SEABLOCK™ (blocking buffer, 1% v/v), 5 mg of $NaN_3$ (0.05% w/v), 5 μL of TWEEN® 20 (surfactant, 0.05% v/v) in 10 mL PBS; other buffers, such as phosphate-buffered saline (PBS, 138 mM NaCl, 2.7 mM KCl, 10 mM $Na_2HPO_4$, 1.8 mM $KH_2PO_4$), 2-(N-morpholino)ethanesulfonic acid buffer (MES buffer, 0.1 M), and sodium bicarbonate (1 M); density media, such as HISTOPAQUE®-1119 (a combination of polysucrose and sodium diatrizoate) (Cat. No. 11191-100 mL) from Sigma Aldrich Corp. (St. Louis, Mo.); and a dissociation buffer for clinical samples, such as 1 M HCl, 1 M NaOH/0.5 M HEPES (4-(2-hydroxyethyl)-1-piperazineethanesulfonic acid). In order to separate the bacterial and viral proteins from the human antibodies in serum samples, 1 M solution of HCl was incubated in 1:1 volume with each sample for about 20 minutes at room temperature. The sample was quenched with 1:1 volume of 1 M NaOH/0.5 M HEPES buffer and allowed to stabilize for about 5 minutes.

Silica Beads Functionalization

Twenty mg of 1 μm carboxylated silica beads were washed with 1000 μL of 0.1M MES buffer twice, sonicated for 20 minutes, washed twice with MES buffer, and resuspended in 800 μL of MES buffer. Ten mg each of EDC and NHS were dissolved in 200 μL of MES buffer, added to the washed silica beads, and allowed to incubate for 30 minutes at 25° C. with continuous rotation. The beads were washed twice with 1 mL of MES buffer, twice with 1 mL of PBS, and resuspended in 900 mL of PBS. One hundred mg of $NaHCO_3$, and 20 mg of desalted antibody were added to reaction and allowed to incubate overnight at 4° C. with continuous rotation. After two washes with PBS, the beads were blocked with 3% SEABLOCK™ (blocking buffer) at 25° C. with continuous rotation for 60 minutes, washed with wash buffer, and resuspended in 100 μL of wash buffer. The beads can be stored in wash buffer at 4° C. for up to six months.

Antibody Labeling with Fluorophore

Using a 100-kDa filter, the antibody was concentrated to 10 mg/mL. Forty-five μL of PBS and 5 μL of $NaHCO_3$ (0.1 M) were added to concentrated antibody. Five μL of stock ALEXA FLUOR® 488 (fluorescent dye) Fluorescent microspheres (9.51E+12 spheres/mL) were mixed with 5 μL of DMSO; 10 μL of the resultant mixture were added to detection antibody solution and incubated for two hours at 25° C. with continuous rotation. The reaction was eluted with a ZEBA™ (polypropylene desalting column) 7-kDa column based on manufacturer's protocol, and the eluent was measured at an absorbance of 280 nm (A280) and 488 nm (A488) to determine the degree of labeling. The concentrated fluorophore-labeled antibody could be stored in 1% v/v SEABLOCK™ (blocking buffer)/PBS solution at 4° C. for up to six months. The antibody diluted to a working concentration had to be prepared daily.

Microfluidic Disc Set-Up

The discs were designed in AutoCAD and fabricated from three layers: a layer of pressure-sensitive double-sided adhesive (Prod. No. 3M™ 9474LE double coated tape with laminating adhesive 300LSE, 12×12; 3M Co., St. Paul, Minn.) sandwiched between two plastic sheets (cast acrylic PD-15401710, 0.060×12×24, McMaster-Carr Supply Co., Atlanta, Ga.). The top plastic layer contained fluid access and vent openings, while the channels were cut in the adhesive layer. The bottom layer of the disc contains no openings. VERSALASER® (VLS) 6.60, 60 Watt (Universal Laser Systems, Inc., Scottsdale, Ariz.) was used to draw the pattern in layers. The discs were manually assembled and the layers were pressed together using a Richeson Baby Press (Jack Richeson & Co., Kimberly, Wis.). The total final volume of each of the 21 wells on the disc was 15 µL.

Fluorescence Microscopy

Images were obtained on a fluorescent microscope Nikon Inverted Microscope Eclipse Ti (Nikon Corp., Melville, N.Y.). A microscope lens with 10× magnification and an exposure time of 40 milliseconds were used throughout all experiments. The excitation and emission wavelengths were 495 and 519 nm, respectively. An area of 1,000,000 pixels (0.5 mm$^2$, approximately the entire bead area) was designated as "reading area" to record the mean intensity of each sample. The mean intensities of three replicas of each sample were collected and averaged to determine the average values and standard deviation of samples.

Assay Design

Silica beads functionalized with capture antibody were incubated with protein of interest in ten-fold serial dilutions in human whole blood for 12 minutes. A detection antibody labeled with ALEXA FLUOR® 488 (fluorescent dye) fluorophore was added to each reaction at a concentration of 60 nM and allowed to incubate for additional 10 minutes, thereby forming a detectable target-bead complex (e.g., as shown in FIG. 1D). A density gradient media (HISTOPAQUE®-1119 (combination of polysucrose and sodium diatrizoate), 3 µL) was applied to each well and briefly spun. After incubation, 5 µL of the reaction volume (in 3 replicas) were dispensed into wells on a disc, and the disc was spun at 5000 RPM for 45 seconds. Additional details are provided in, e.g., Litvinov J et al., "Centrifugal sedimentation immunoassays for multiplexed detection of enteric bacteria in ground water," *Biomicrofluidics* 2016; 10(1):014103 (9 pp.); Koh C Y et al., "Centrifugal microfluidic platform for ultrasensitive detection of botulinum toxin," *Anal. Chem.* 2015; 87(2):922-8; and Schaff U Y et al., "Whole blood immunoassay based on centrifugal bead sedimentation," *Clin. Chem.* 2011; 57(5):753-61.

In one instance, an analyte of interest in serial dilutions can be added to the beads with a capture antibody. The reaction can be allowed to proceed (e.g., for 12 minutes). Then, a detection antibody can be added (e.g., and incubated for 10 minutes). The disc can be spun, thereby forcing the beads with attached analyte and detection antibody to pass through the density gradient, while unreacted analyte and detection antibody are trapped inside the density gradient. The fluorescent signal from the detection antibody attached to beads through analyte can be quantified by fluorescent microscopy.

Statistical Analysis

The average background fluorescence signal (n=3, mean intensity of silica beads with capture antibody only, without analyte and detection antibody) was subtracted from the collected individual raw data points. The average value of the signal intensity for every protein or antibody concentration was calculated. To normalize the data, all the averaged values were divided by the averaged fluorescence intensity of the highest protein or antibody concentration. The standard deviation was determined by calculating the square root of the sum of squared standard deviations of background and averaged data points. The error bars represent ±1 standard deviation.

KaleidaGraph software was used for curve fitting and determining of limit of detection (LOD), limit of quantification (LOQ), $R^2$ values, and chi-squared values. Percentage error (0.1%) and first-degree parameter partial derivatives were allowed for calculations purposes. All curves are represented as sigmoidal fit with $R^2$ values that are higher than 0.98. The limit of detection and the limit of quantification were set as three and ten standard deviations, respectively, higher than the signal for negative control sample, which included functionalized silica beads incubated with corresponding fluorescently labeled antibody but without the analyte of interest.

Example 3: Centrifugal Microfluidic Platform for Rapid, Multiplexed Detection of TB and HIV Biomarkers in Serum Samples Tuberculosis (TB) is an infectious disease caused by aerobic bacteria of the *Mycobacterium tuberculosis* complex. It is spread through the air from the lungs of infected persons during coughing or sneezing with the infectious dose being only a few bacteria. However, in many cases, the infection is latent and cannot be transmitted. In some cases, the infection becomes acute and can be spread from person to person (see, e.g., Aaron L et al., "Tuberculosis in HIV-infected patients: a comprehensive review," *Clin. Microbiol. Infect.* 2004; 10(5):388-98).

One of the causes for latent TB to develop into acute TB is its combination with an impaired immune system, very often, as a result of human immunodeficiency virus (HIV) infection (see, e.g., Lawn S D et al., "Epidemiology of HIV-associated tuberculosis," *Curr. Opin. HIV AIDS* 2009; 4(4):325-33). Infection with HIV can lead to an increased risk of developing, re-appearing, or having a re-infection with TB shortly after the onset of HIV infection, with risks increasing, as a patient becomes increasingly immunodeficient (see, e.g., Wood R et al., "Risk factors for developing tuberculosis in HIV-1-infected adults from communities with a low or very high incidence of tuberculosis," *J. Acquir. Immune Defic. Syndr.* 2000; 23(1):75-80; and Hermans S M et al., "The timing of tuberculosis after isoniazid preventive therapy among gold miners in South Africa: a prospective cohort study," *BMC Med.* 2016; 14:45 (11 pp.)). The two diseases accelerate each other to form a lethal outcome (see, e.g., Getahun H et al., "HIV infection-associated tuberculosis: the epidemiology and the response," *Clin. Infect. Dis.* 2010; 50 Suppl 3:S201-7).

Currently, it is estimated that as much as one-third of world's population that is infected with HIV is also co-infected with TB (see, e.g., International Federation of Red Cross and Red Crescent Societies, "The link between tuberculosis and HIV," available at ifrc.org/en/what-we-do/health/diseases/tuberculosis/the-link-between-tuberculosis-and-hiv/(last accessed Jun. 30, 2016)). Infection with TB is the leading cause of mortality among HIV-infected patients. According to the World Health Organization, 25% of fatalities among people infected with HIV are due to the TB disease (see, e.g., World Health Organization, "News release: Tuberculosis," *Saudi Med. J.* 2013; 34(11):1205-7). The CDC has reported that infection with HIV is the major factor for transforming latent TB infection into an active disease (see, e.g., Centers for Disease Control and Prevention, "Recommendations for Human Immunodeficiency Virus (HIV) screening in tuberculosis (TB) clinics," available at cdc.gov/tb/publications/factsheets/testing/hivscreening.htm (last accessed Jun. 30, 2016, last updated Dec. 12, 2014)).

Co-infection poses a great challenge to the diagnosis and treatment of both diseases. For example, when detecting TB using IFN-γ assay in HIV-infected patients, the assay might produce a false-negative or indeterminate result due to low production of IFN-γ proteins in HIV-positive patients. In early stages during HIV infection, there is a noticeable decrease in production of IFN-γ and CD4+ cells, which can also lead to an increased risk of latent TB infection to advance to an acute infection (see, e.g., Ottenhoff T H et al., "Novel human immunodeficiencies reveal the essential role of type-I cytokines in immunity to intracellular bacteria," *Immunol. Today* 1998; 19(11):491-4; and du Toit L C et al., "Tuberculosis chemotherapy: current drug delivery approaches," *Respir. Res.* 2006; 7:118 (18 pp.)).

The active TB, in its turn, infects alveolar macrophages and limits the ability of the body's defense system to effectively contain its growth. The co-infection increases both viral and bacterial replication (see, e.g., Pathak S et al., "Effects of in vitro HIV-1 infection on mycobacterial growth in peripheral blood monocyte-derived macrophages," *Infect. Immun.* 2010; 78(9):4022-32). The increase of viral load on macrophages and other immune cells co-infected with both HIV and TB results in acute TB due to the existing HIV infection, increasing the morbidity and the mortality of the infected patients (see, e.g., Diedrich C R et al., "HIV-1/*Mycobacterium tuberculosis* coinfection immunology: how does HIV-1 exacerbate tuberculosis?," *Infect. Immun.* 2011; 79(4):1407-17; and Baba K et al., "Evaluation of immune responses in HIV infected patients with pleural tuberculosis by the QuantiFERON TB-Gold interferon-gamma assay," *BMC Infect. Dis.* 2008; 8:35 (8 pp.)).

Currently available diagnostic assays can detect either HIV or TB with high sensitivity and specificity, but in order to differentiate between latent and active stages of TB, strategically different assays need to be developed. The existing diagnostic assays are based on host immune response and have to be performed and analyzed simultaneously (see, e.g., Centers for Disease Control and Prevention, "Laboratory testing for the diagnosis of HIV infection: updated recommendations," Jun. 27, 2014 (68 pp.), available at dx.doi.org/10.15620/cdc.23447 (last accessed Jun. 30, 2016)).

Many HIV detection tests are available. One platform includes an ELISA format for the detection of HIV antibodies as soon as 2 to 12 weeks after onset of infection and for the detection of p24 antigen in blood as soon as 3 to 28 days. The two rapid tests are available for the HIV antibody detection in whole blood or saliva. Unlike the ELISA and rapid tests, nucleic acids amplification tests (NAAT) detect genetic material (RNA) of the virus instead of antibodies. Unfortunately, in addition to NAAT being very expensive, they can also produce false-positives (see, e.g., HIV InSite, "What kinds of HIV screening tests are available in the United States?," Aug. 3, 2011, available at hivinsite.ucsf.edu/insite?page=basics-01-01 (last accessed Jun. 30, 2016)).

Differentiating between latent and active infections can be challenging. For instance, a TB skin or blood test does not differentiate between latent and active infections. While a TB skin test might have a false positive result due to prior BCG immunizations, the INF-γ Release Assay (IGRA) is independent of whether a person was BCG-immunized (see, e.g., Sultan B et al., "Comparison of two interferon-gamma release assays (QuantiFERON-TB Gold In-Tube and T-SPOT.TB) in testing for latent tuberculosis infection among HIV-infected adults," *Int. J. STD AIDS* 2013; 24(10):775-9; Ramos J M et al., "Contribution of interferon gamma release assays testing to the diagnosis of latent tuberculosis infection in HIV-infected patients: a comparison of QuantiFERON-TB Gold In Tube, T-SPOT.TB and tuberculin skin test," *BMC Infect. Dis.* 2012; 12:169 (10 pp.); and Pullar N D et al., "HIV patients with latent tuberculosis living in a low-endemic country do not develop active disease during a 2 year follow-up; a Norwegian prospective multicenter study," *BMC Infect. Dis.* 2014; 14:667 (10 pp.)). The IGRA can also give less false negatives. However, a positive IGRA result only suggests that there is a bacterial infection and does not differentiate whether it is latent or active. In addition, the IGRA test is not accurate in people infected with HIV since the test checks for T-cell secreted proteins (IFN-γ) that are decreased during the ongoing HIV infection (see, e.g., Cheallaigh C N et al., "Interferon gamma release assays for the diagnosis of latent TB infection in HIV-infected individuals in a low TB burden country," *PLoS One* 2013; 8(1):e53330 (7 pp.); Pandie S et al., "Diagnostic accuracy of quantitative PCR (Xpert MTB/RIF) for tuberculous pericarditis compared to adenosine deaminase and unstimulated interferon-γ in a high burden setting: a prospective study," *BMC Med.* 2014; 12:101 (11 pp.); and Pooran A et al., "Different screening strategies (single or dual) for the diagnosis of suspected latent tuberculosis: a cost effectiveness analysis," *BMC Pulm. Med.* 2010; 10:7 (14 pp.)).

Many advances have been made to detect HIV and TB simultaneously in blood samples. Usually, as publications suggest, the assays have low accuracy. In general, many assays can provide qualitative results, but not a semi-quantitative measurement that could be used to deduce the course of infection. For example, Corstjens et al. (Corstjens P L et al., "Rapid assay format for multiplex detection of humoral immune responses to infectious disease pathogens (HIV, HCV, and TB)," *Ann. NY Acad. Sci.* 2007; 1098:437-45) developed a lateral flow multiplexed immunoassay for HIV, TB, and hepatitis C virus (HCV) detection with high specificity but low sensitivity and accuracy. The problems with sensitivity were exhibited when tests were performed on samples from immuno-compromised individuals and children, i.e., patients who usually show low reactivity to antibody screening assays.

A possible solution to the problem of TB detection in HIV-positive individuals could be to detect secreted bacterial proteins, which will indicate actively reproducing bacteria. The detection of elevated numbers of secreted proteins or toxins would be the direct indication of an active infection. This strategy bypasses the problem of depending on the host immune response (which is likely not working properly in active HIV infection) to make a diagnosis of infection.

Ag85B and 38-kDa represent such proteins in tuberculosis infection (see, e.g., Landowski C P et al., "Combinatorial use of antibodies to secreted mycobacterial proteins in a host immune system-independent test for tuberculosis," *J. Clin. Microbiol.* 2001; 39(7):2418-24). Both proteins impair host immunity by inactivating CD4 and CD8 T-cells. The Ag85 complex is responsible for adherence and dissemination of TB inside the host as well as for cell wall synthesis (see, e.g., Armitige L Y et al., "Disruption of the genes encoding antigen 85A and antigen 85B of *Mycobacterium tuberculosis* H37Rv: effect on growth in culture and in macrophages," *Infect. Immun.* 2000; 68(2):767-78). The 38-kDa protein is a phosphate binding protein that serves as an initial receptor for active transport (Chang Z et al., "The immunodominant 38-kDa lipoprotein antigen of *Mycobacterium tuberculosis* is a phosphate-binding protein," *J. Biol. Chem.* 1994; 269 (3):1956-8; and Jung S B et al., "The mycobacterial 38-kilodalton glycolipoprotein antigen activates the mitogen-activated protein kinase pathway and release of proinflammatory cytokines through Toll-like receptors 2 and 4 in human monocytes," *Infect. Immun.* 2006; 74(5):2686-96). The Ag85 complex can account for 30% of the total secreted proteins of TB, and the 38-kDa protein accounts for another 10%. In addition, the Ag85 complex can be detected in HIV-positive patients with high specificity (see, e.g., Steingart K R et al., "Performance of purified antigens for serodiagnosis of pulmonary tuberculosis: a meta-analysis," *Clin. Vaccine Immunol.* 2009; 16(2):260-76; Uma Devi K R et al., "Antibody response to *Mycobacterium tuberculosis* 30 and 16 kDa antigens in pulmonary tuberculosis with human immunodeficiency virus coinfection," *Diagn. Microbiol. Infect. Dis.* 2003; 46(3):205-9; and Raja A et al., "Improved diagnosis of pulmonary tuberculosis by detection of free and immune complex-bound anti-30 kDa antibodies," *Diagn. Microbiol. Infect. Dis.* 2004; 50(4):253-9).

The detection of bacterial and viral proteins can be more reliable, as compared to the detection of antibodies and can be directly correlated to the number of reproducing bacteria and viruses (see, e.g., McNerney R et al., "Towards a point-of-care test for active tuberculosis: obstacles and opportunities," *Nat. Rev. Microbiol.* 2011; 9(3):204-13). For example, a single HIV virus has 2,000 copies of the p24 protein (or 1 pg of p24 corresponds to 10,000 HIV virus particles) (see, e.g., "HIV," available at web-books.com/eLibrary/Medicine/Infectious/AIDS_HIV.htm (last accessed Jun. 30, 2016)). Thus, the quantitative detection of p24 protein and viral load can result in placement of patient on the timeline of the initial HIV infection in order to achieve a better understanding of the onset time of TB.

Unfortunately, most cases of TB in HIV-infected patients occur in the developing countries, where people have to travel significant distances to reach clinics if symptoms persist. The test should be quick and easy to perform for personnel at the location and should give a screening result without the patient having to come back for additional appointments. Until recently, according to McNerney et al. (*Nat. Rev. Microbiol.* 2011; 9(3):204-13), there were no tests that can compare to sputum smear microscopy and, in addition to long analysis time of each smear, such tests required a microscopy abilities and a skilled technician. However, many advances in analytical techniques were made and the Cepheid GENEXPERT® (cartridge-based system) MTB test now allows for detection of *M. tuberculosis* directly from sputum sample within 3-4 hours. It was approved by FDA and is claimed to be more sensitive than smear analysis (U. S. Food and Drug Administration, "News release: New data shows test can help physicians remove patients with suspected TB from isolation earlier," Feb. 12, 2015, available at fda.gov/NewsEvents/Newsroom/PressAnnouncements/ucm434226.htm (last accessed Jun. 30, 2016)). An already established PCR detection of *M. tuberculosis*, though rather expensive, is also very sensitive and requires about two hours to complete and is being used in remote locations in resource-poor settings.

Here, we show the development of an ELISA-like multiplexed centrifugal sedimentation assay for detection of *Mycobacterium tuberculosis* secreted proteins and HIV p24 protein along with antibodies in human whole blood. The assay was validated in samples spiked with protein of interest in presence of HIV-related protein and antibodies. For the proof of concept, the assay was also validated in clinical serum samples. The assay has a limit of detection lower than the regular ELISA, while having an advantage of detecting multiple proteins and antibodies from one blood sample within 30 minutes.

Results and Discussion

The basic principle of the centrifugal microfluidic assay is that centrifugal force propels the liquid from the center of the disc towards the rim of the disc during spinning. This centrifugal movement requires only a simple motor to rotate the disc and to move the fluid in one direction. The entire assay is performed on a single disc without the need of centrifuges, external pumps, or any other additional equipment. The fluid movement inside the microfluidic disc does not depend on ionic strength or pH of solution. Rather, the movement of the reagents inside the disc' wells depends only on the principle that heavier particles will move further through the gradient than lighter particles, depending on the density and viscosity of the density gradient.

The heaviest particles, in our case, the carboxylated silica beads with analyte, capture antibody, and detection antibody will move through the density gradient all the way to the tip of the well at the rim of the disc. The unreacted reagents, excess analyte, and detection antibodies will be left behind the density gradient since their density is less than the density of the gradient. This approach of moving reagents through the gradient allows adding all assay components to the disc simultaneously and performing an assay without the washes between different steps. The density gradient acts like a wash, removing the non-specific binding and eliminating false-positives. The sample, being pushed through the gradient, experiences friction forces, helping it to eliminate the non-specific attachments and retain only the covalently bonded and specific ones.

The centrifugal microfluidics approach becomes very useful especially when working with whole blood samples. One of the biggest pros is that absolutely no sample preparation or cleanup is necessary. Whole blood can be pipetted to the disc as is, without prior separation steps, which are done directly on the disc while the disc is spinning. When a 10 μL sample of whole blood after a 20-minute incubation with analyte of interest, capture beads, and detection antibodies is pipetted onto a disc, the only remaining step is to turn the motor on and spin the disc. The reagents will separate according to their density. The beads with capture antibody, bound analyte, and detection antibody (still being the heaviest particles) will spin all the way through the density gradient to the tip of the well, leaving behind the unreacted reagents and the rest of the blood sample separated into fractions. The red blood cells will be right at the top of density gradient, followed by the white blood cells closer to the center of the disc, followed by other fluids leftovers from density gradient, beads, and detection antibody, closest to the center of the disc.

To have an insight on how advanced TB disease is progressing in a specific patient, one can evaluate the type of secreted proteins as well as their amounts. For example, the Ag85 complex appears as the first sign of an active TB, while appearance of the 38-kDa protein indicates advanced or established disease (see, e.g., Espitia C et al., "A 38-kD *Mycobacterium tuberculosis* antigen associated with infection: its isolation and serologic evaluation," *Clin. Exp. Immunol.* 1989; 77(3):373-7; and Daniel™ et al., "The serodiagnosis of tuberculosis and other mycobacterial diseases by enzyme-linked immunosorbent assay," *Am. Rev. Respir. Dis.* 1987; 135(5):1137-51). Also, the Ag85 complex can be detected in culture media as early as 2-4 days, much earlier than the antibodies at detectable levels start being produced. Keeping in mind that the survival of patients with advanced HIV infection and onset of active TB may only be measured in days or weeks, the earliest possible detection of acute TB is crucial (see, e.g., Young D B et al., "Confronting the scientific obstacles to global control of tuberculosis," *J. Clin. Invest.* 2008; 118(4):1255-65).

Preliminary experiments were performed in different batches of single donor human whole blood (Cat. No. IPLA-WB1, Innovative Research Inc., Novi, Mich.). All blood was tested and found negative or non-reactive by Innovative Research Inc. using FDA-approved methods. Due to limitation of pending testing, the blood was received only on the third day after drawing. Upon receipt, the blood was aliquoted into 1 mL volumes and stored at 4° C. Before each experiment, it was allowed to normalize to room temperature for 30 minutes. All blood had 10% sodium citrate as an anticoagulant.

To reduce the error of the quantitative analysis, no data imaging software was used for signal quantification. Mean intensity of almost the entire tip area (0.5 mm$^2$) that was designated as reading area, was recorded for all samples. The images were acquired at room temperature. The raw data was then averaged, subtracted background, and normalized. No significant photobleaching was observed throughout our experiments, due to use of a relatively photostable dye (ALEXA FLUOR® 488, fluorescent dye), a short exposure time (40 milliseconds), a large working distance (7.5 mm), and illumination of samples through a 10× (low-power) objective. The exposure of samples to the light was minimized to 1-2 seconds during focusing. Standard excitation intensity, as well as standard gain and power were used in all experiments.

Single Protein Detection

Figure 4A:
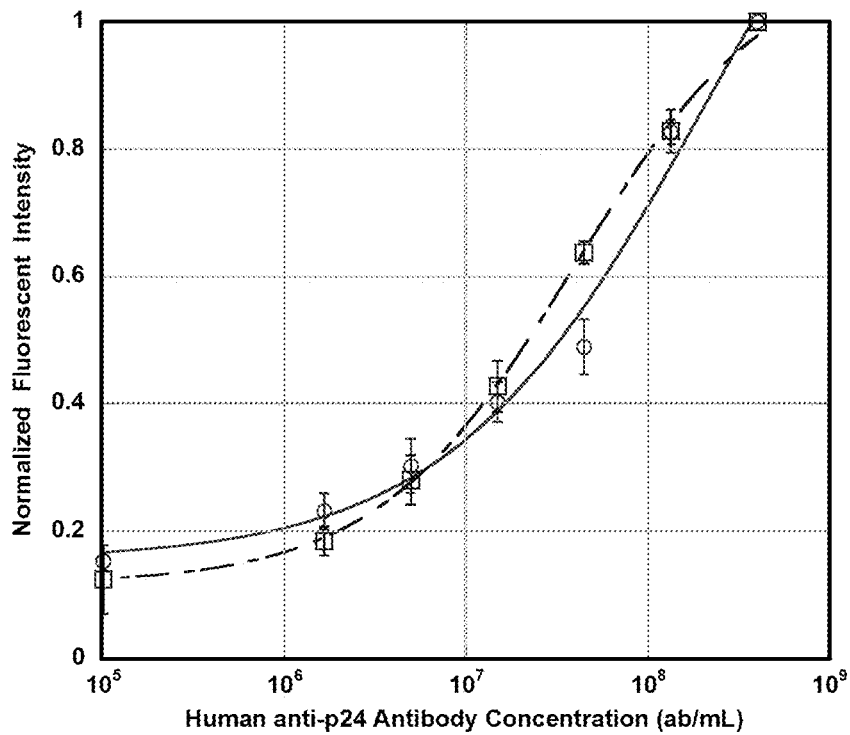
FIG. 4A-4D shows single detection (circles) and multiplexed detection (squares) of human anti-HIV p24 antibody, which is a host-responsive protein produced in response to an HIV infection (FIG. 4A); HIV p24 protein, which is a non-host viral capsid protein (FIG. 4B); tuberculosis (TB) 38-kDa protein, which is a non-host bacterial antigenic lipoprotein (FIG. 4C); and TB Ag85B protein, which is a non-host bacterial transferase protein (FIG. 4D). The analyte of interest was spiked into human whole blood and reacted with its corresponding capture particles for 12 minutes. After incubation with the corresponding detection antibody for 10 minutes, the reaction was added to the disc with a density gradient. Subsequent spinning at 5000 RPM allowed for separation between bound analytes (to capture beads) and unbound reactants (e.g., detection antibody). Fluorescence signal was detected and quantified at the bead area at the tip of the channel.
Figure 4B:
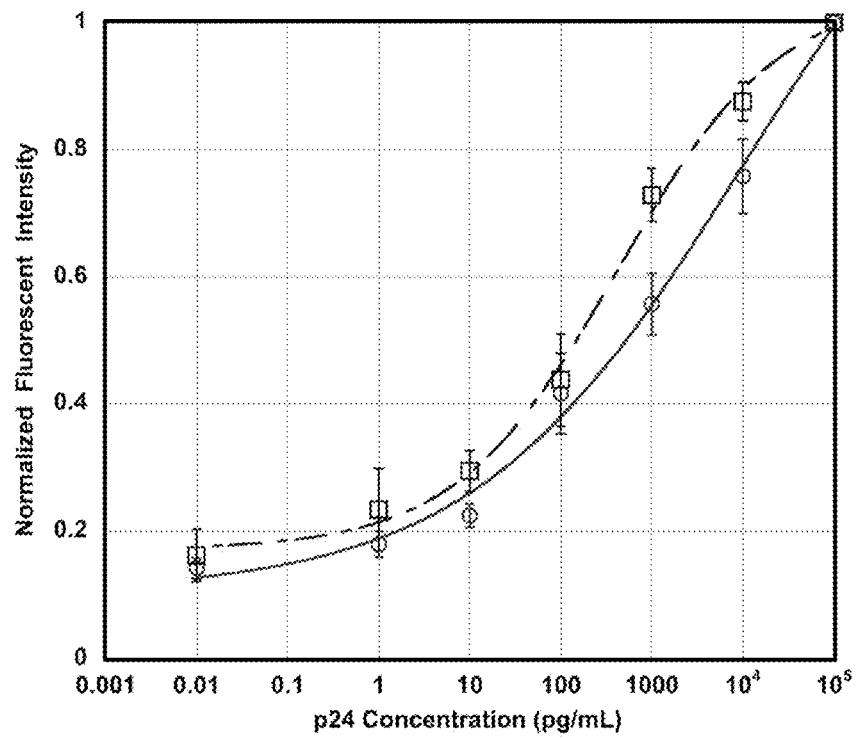

Various proteins of interest were detected. For proteins and antibodies related to an HIV infection, we detected the HIV p24 protein and human anti-p24 antibody produced by the host in response to an infection. For the detection of human polyclonal anti-p24 HIV antibodies, human p24 protein was used as capture and mouse anti-human (Fc) antibodies were used for detection (FIG. 4A). For the detection of HIV p24 protein, purified human polyclonal anti-p24 antibody was used for capture and antibody clone 9072 was used for detection (FIG. 4B).

Figure 4C:
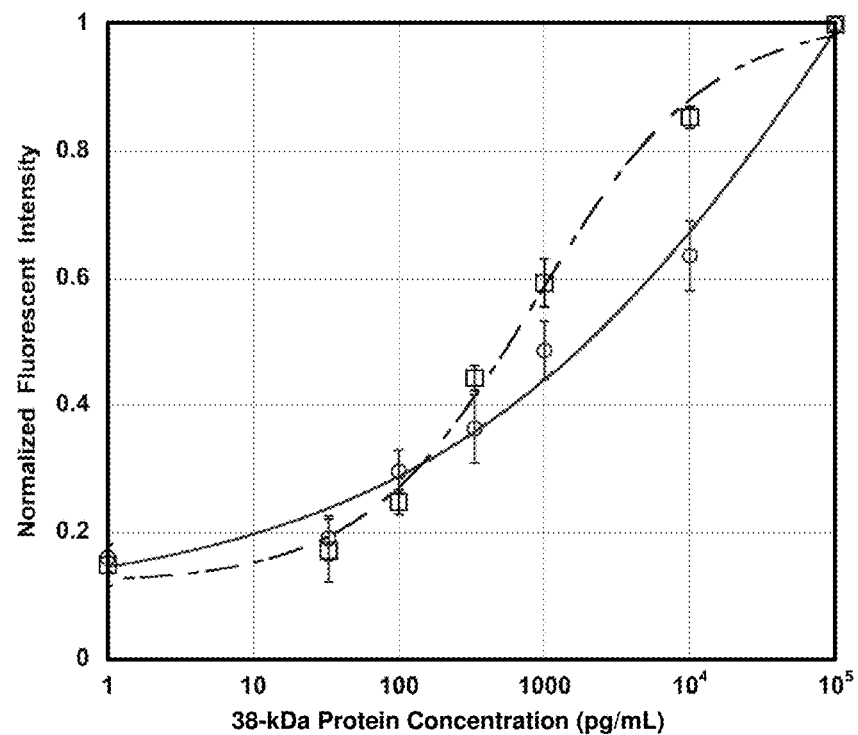
Figure 4D:
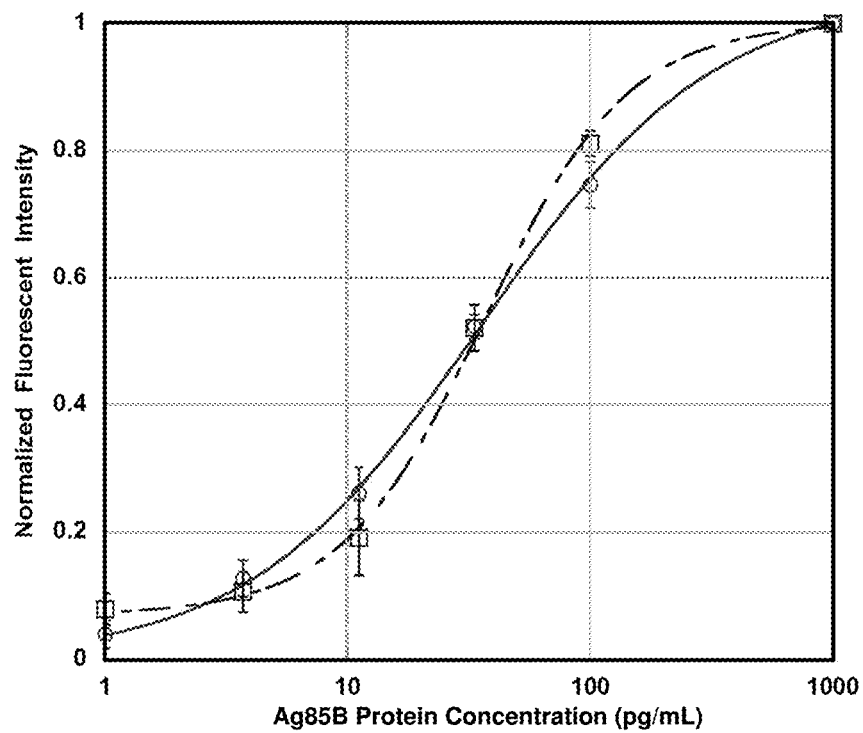

For proteins related to a TB infection, we detected the TB 38-kDa protein and the TB Ag85B protein. For the detection of 38-kDa protein, antibody clone HTM82 was used for capture and antibody clone HTM81 was used for detection (FIG. 4C). For the detection of Ag85B protein, the same polyclonal anti-Ag85B antibody was used for capture and detection (FIG. 4D).

Protein of interest was spiked into blood in 10-fold dilution series. All proteins were ten-fold serially diluted starting at the concentration 1 ng/mL and purified polyclonal human anti-p24 antibody was diluted three-fold starting at the concentration of 6.7 nM (4×108 antibodies/mL).

Multiplexed Protein Detection

Experiments for multiplexed detection were performed on the same day in the same batches of blood as the single protein detection. For every analyte of interest, a mix of other analytes was added each at a concentration 1 ng/mL per reaction. For example, for the multiplexed detection of Ag85B protein, the human anti-p24 antibody, 38-kDa and p24 proteins were added to each sample including the negative control. The assays were performed as described herein, and the results were analyzed with fluorescent microscope.

Various limits were determined for multiplexed detection of a particular target analyte. Determined limits included a limit of detection (LOD) and a limit of quantification (LOQ) for the following: an LOD of 3.12 pg/mL and an LOQ of 12.95 pg/mL for the single p24 detection; an LOD of 6.93 pg/mL and an LOQ of 23.07 pg/mL for multiplexed p24 detection; an LOD of 24.56 pg/mL and an LOQ of 146.91 pg/mL for single 38-kDa protein detection; an LOD of 53.32 pg/mL and an LOQ of 168.16 pg/mL for multiplexed 38-kDa protein detection; an LOD of 3.11 pg/mL and an LOQ of 10.25 pg/mL for single Ag85B protein detection; an LOD of 7.53 pg/mL and an LOQ of 18.76 pg/mL for multiplexed Ag85B protein detection; an LOD of 7.31e5 ab/mL and an LOQ of 6.26e6 ab/mL for single human anti-p24 antibody detection; and an LOD of 5.62e6 ab/mL and an LOQ of 5.16e7 ab/mL for multiplexed human anti-p24 antibody detection (see FIG. 4A-4D).

Clinical Data Analysis

Frozen de-identified serum samples previously confirmed to be HIV-positive by ELISA and Western Blot followed by PCR for viral load (n=18) were tested. In addition, HIV-positive serum from one active pulmonary TB-positive case and serum from one TB-positive, HIV-negative case (n=2, confirmation of TB by PCR from sputum) were tested. Each sample was analyzed for presence of human anti-HIV antibodies, HIV p24 protein, bacterial 38-kDa protein, bacterial Ag85B protein, human anti-38-kDa antibody, and human anti-Ag85B antibody using the same reagents as in spiked samples.

Each sample was treated with buffer to separate the antibodies from proteins as described herein (e.g., see Example 2). The sample then was serially diluted 10-fold with wash buffer, and the assay was performed as described herein (e.g., see section entitled "Single protein detection"). The negative control samples represented samples that were HIV-negative, as confirmed by PCR and TB-negative based on clinical picture. The negative control for the NTC samples were the assays run in buffer. The specificity of the assay for HIV detection was 7/8 (87.5%), and the sensitivity was 18/20 (90%).

Clinical Data Results

Figure 5:
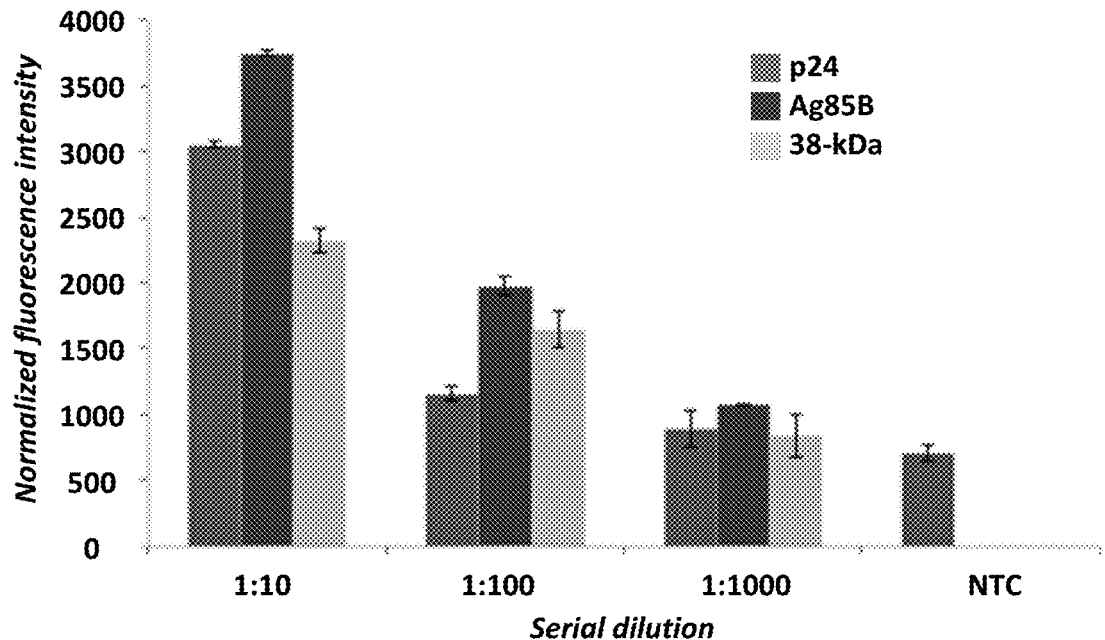
FIG. 5 shows detection of proteins in a sample with TB/HIV co-infection. The sample was treated with HCl/NaOH-HEPES buffers and serially diluted with wash buffer. Then, samples were incubated with capture beads having modified capture antibodies and with corresponding detection antibodies. For p24 capture and detection (data labeled "p24"), the 9072 antibody beads captured the HIV p24 protein from sample, whereas the 9071 antibody served as the detection antibody. For Ag85B capture and detection (data labeled "Ag85B"), anti-Ag85B antibody beads captured the TB Ag85B protein, and the same anti-Ag85 antibody served as the detection antibody. For 38-kDa capture and detection (data labeled "38-kDa"), the HTM82 antibody beads captured the TB 38-kDa protein, whereas the HTM81 antibody served as the detection antibody.

Between the two available samples with TB infection, one had the co-infection with HIV. When analyzing for HIV and TB proteins, the sample dilutions corresponded to the dose-response curve (FIG. 5), and the samples were confirmed to be HIV and TB positive.

Figure 6:
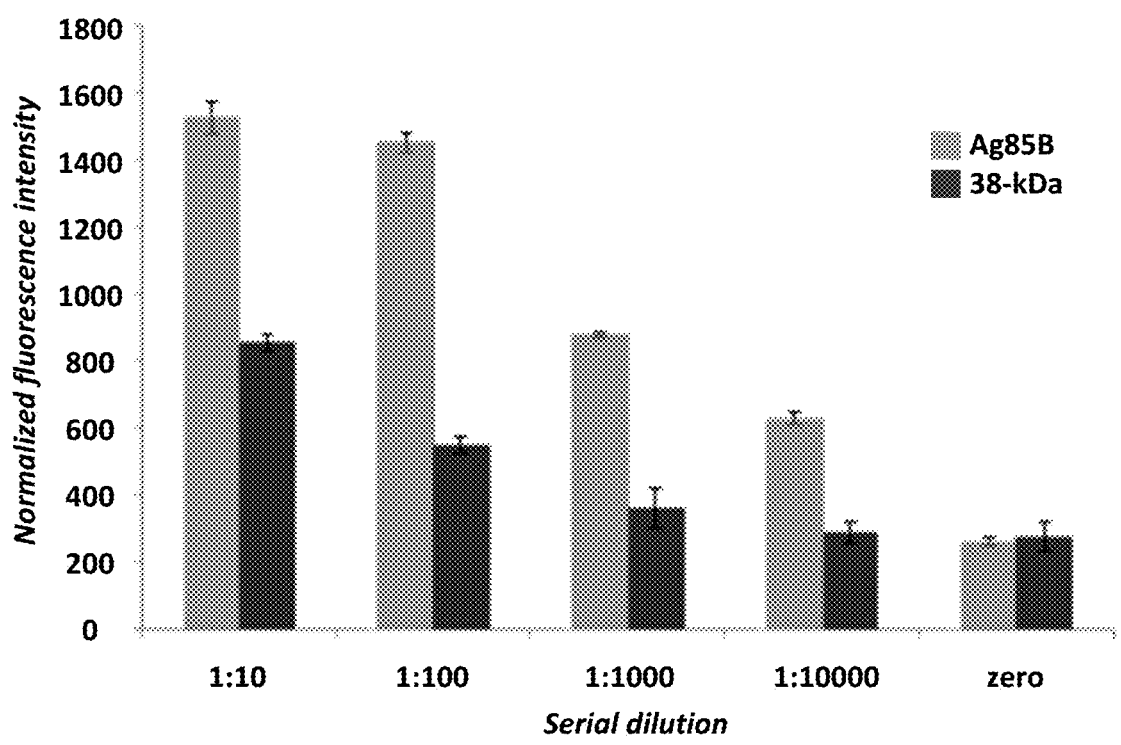
FIG. 6 shows detection of TB proteins in TB-positive/HIV-negative sample. The sample was treated with 1M HCl for 15 minutes and 1M NaOH/HEPES for 5 minutes. The treated sample was serially diluted 10-fold. Detectable TB proteins included Ag85B and 38-kDa. Ten microliters of sample dilutions were incubated with anti-Ag85B antibody beads (data labeled "Ag85B"), and another ten microliters were incubated with anti-38-kDa antibody (HTM82) beads (data labeled "38-kDa") for 10 minutes. Five microliters of detection antibody (anti-Ag85B and HTM81 for Ag85B detection and 38-kDa detection, respectively) were added and allowed to incubate for 10 minutes. The "zero" sample was the TB-negative/HIV-negative sample diluted 1:10.

The second TB-positive sample was HIV-negative (PCR) and showed signal similar to the background signal in assays for HIV detection. The assay for TB protein detection showed a dose-response result (FIG. 6).

Figure 7A:
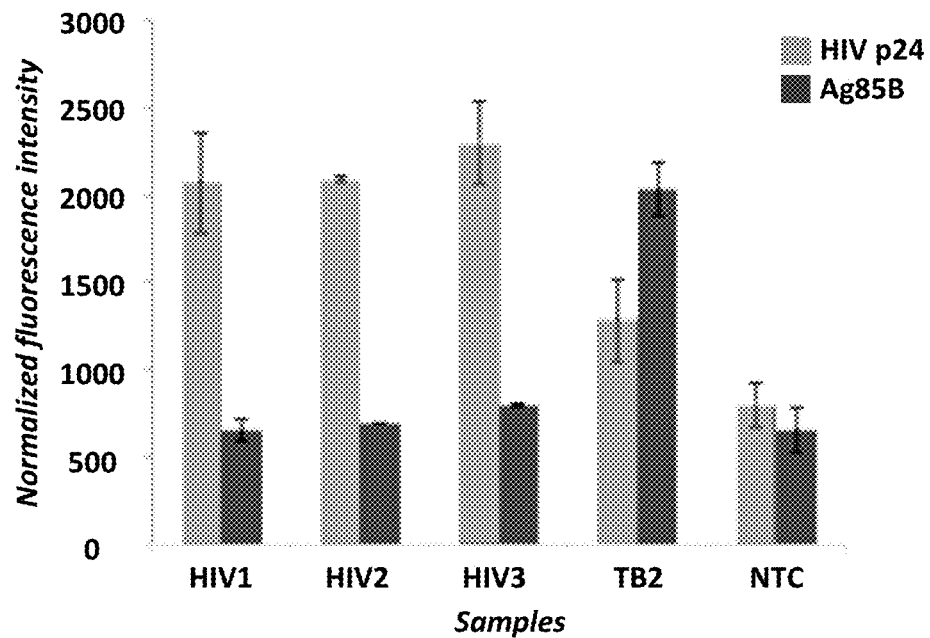
FIG. 7A-7B shows specific and non-specific binding assays for multiplexed detection in HIV and TB samples. Provided are detection of an HIV protein (p24) and a TB protein (Ag85B) within the sample (FIG. 7A) or detection of an HIV antibody (human anti-p24 antibody) and a TB protein (38-kDa) within the sample (FIG. 7B). Three HIV-positive/TB negative samples (labeled "HIV1," "HIV2," and "HIV3") and one TB-positive/HIV-negative samples (labeled "TB2") were treated with HCl/NaOH-HEPES buffers and diluted 1:1000 with wash buffer. All the samples were incubated with beads to detect an HIV protein or HIV antibody (light gray in FIG. 7A-7B) and with beads to detect a TB protein (dark gray in FIG. 7A-7B). When the TB sample was incubated with beads to detect the HIV p24 protein (beads including anti-HIV p24 9072 as the capture antibody and anti-HIV p24 9071 as the detection antibody), the sample showed an elevated signal, compared to a negative control (labeled "NTC") (see data for sample TB2 in FIG. 7A), but not after incubation with beads to detect human anti-p24 antibody (beads including p24 as the capture protein and anti-human IgG antibody as the detection antibody) (see data for sample TB2 in FIG. 7B). The HIV samples did not show cross-reactivity with beads and antibodies configured to detect TB proteins (Ag85B or 39-kDa).
Figure 7B:
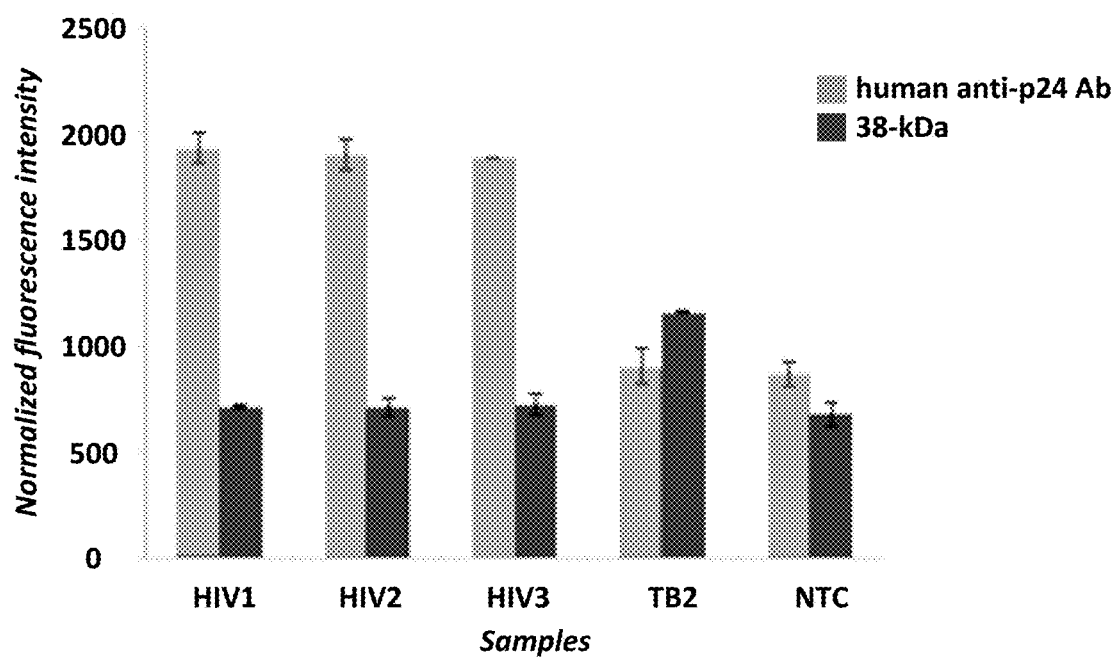

In order to simultaneously detect HIV and TB proteins, negative control experiments were performed to evaluate the cross-reactivity of the detection antibodies (FIG. 7A-7B). Three different HIV-positive samples and one TB-positive sample were treated for protein separation and incubated in a non-specific assay. Each sample was incubated with HIV and TB reagents, such that three HIV samples should be only HIV-positive and that the TB sample should only be TB-positive (sample TB2 was the TB-positive, HIV-negative sample; samples HIV1, HIV2, and HIV3 were the TB-negative, HIV-positive samples). None of the HIV samples showed any cross-reactivity with TB reagents; however, the TB sample showed an elevated background when incubated with 9072 HIV capture antibody (FIG. 7A, light gray bars for sample TB2, as compared to control NTC).

Figure 8:
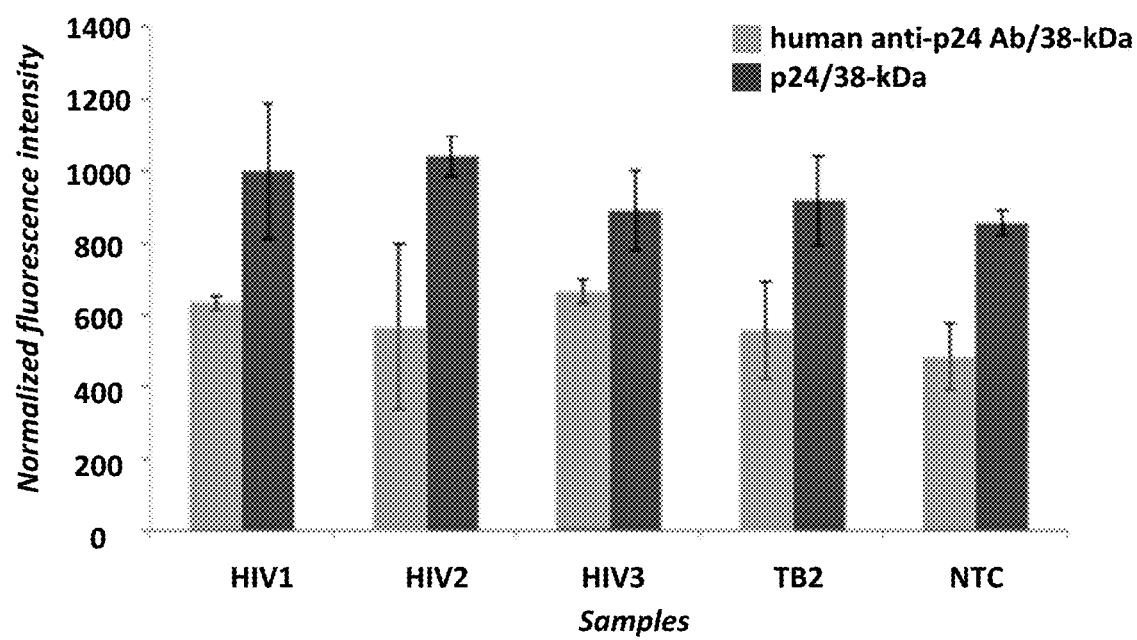
FIG. 8 shows cross-reactivity assays for multiplexed assay tests. A negative control assay was performed on HIV-positive samples. Samples were incubated with beads to detect human anti-p24 antibody (light gray in FIG. 8, using p24 as the capture protein) or to detect HIV p24 protein (dark gray in FIG. 8, using anti-HIV p24 9072 as the capture antibody), as well as detection antibodies for non-specific binding to the TB 38-kDa protein (using HTM81 as the detection antibody). As can be seen, the assay employed beads including 9072 as the capture antibody (dark gray in FIG. 8), and these capture beads cross-reacted with the TB detection antibodies, contributing to a higher background signal. Beads including p24 as the capture protein (light gray in FIG. 8) did not cross-react with the TB detection antibodies. Provided are data for HIV-positive samples (labeled "HIV1," "HIV2," and "HIV3"), a TB-positive/HIV-negative sample (labeled "TB2"), and a negative control (labeled "NTC").

Further negative control experiments (FIG. 8) were conducted on the HIV-positive samples to confirm the antibody cross-reactivity seen in FIG. 7A-7B. HIV capture beads modified with p24 protein and HIV 9072 antibodies were incubated with HIV-positive samples, and an HTM81 TB detection antibody was added in both cases. As shown in FIG. 8, the elevated background independent of dose-response curve existed when 9072 HIV capture beads were incubated with HTM 81 TB detection antibodies, thereby confirming cross-reactivity.

Figure 9A:
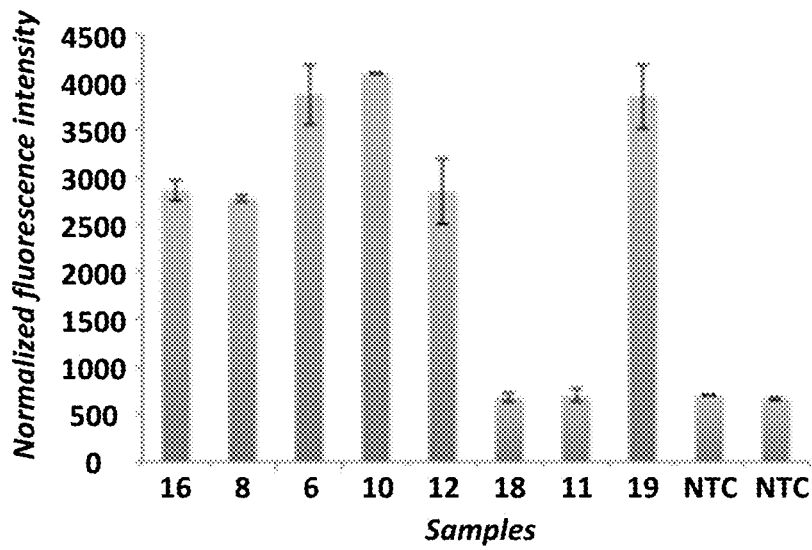
FIG. 9A-9B shows detection of the HIV p24 protein in HIV-positive samples. Out of 19 HIV-positive samples, p24 protein was detected in 16 samples. One of the samples had red blood cells lysed and was not used. Two samples (18 and 11) showed a false-negative signal for p24 protein detection. Assays were conducted with beads using anti-HIV p24 9072 as the capture antibody and anti-HIV p24 9071 as the detection antibody. Provided are data for HIV-positive samples (labeled numerically) and negative control (labeled "NTC," "NTC1," or "NTC2").
Figure 9B:
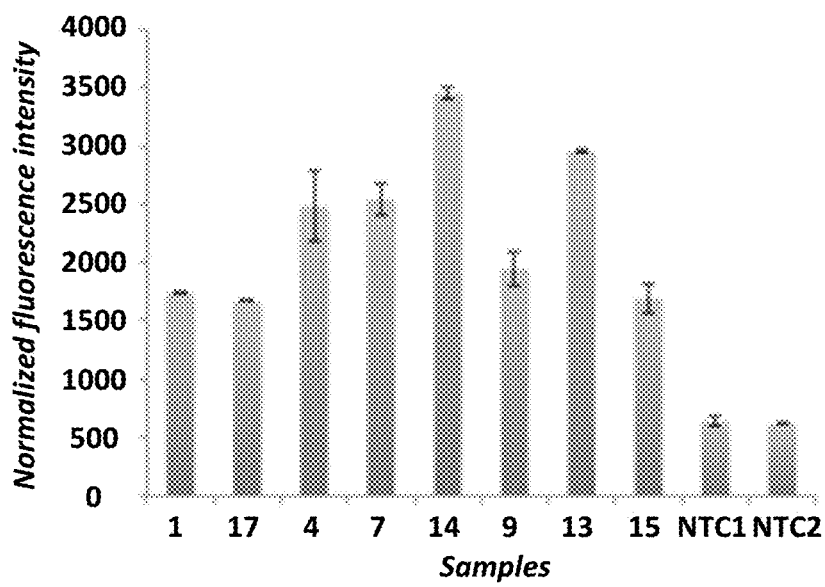
Figure 10A:
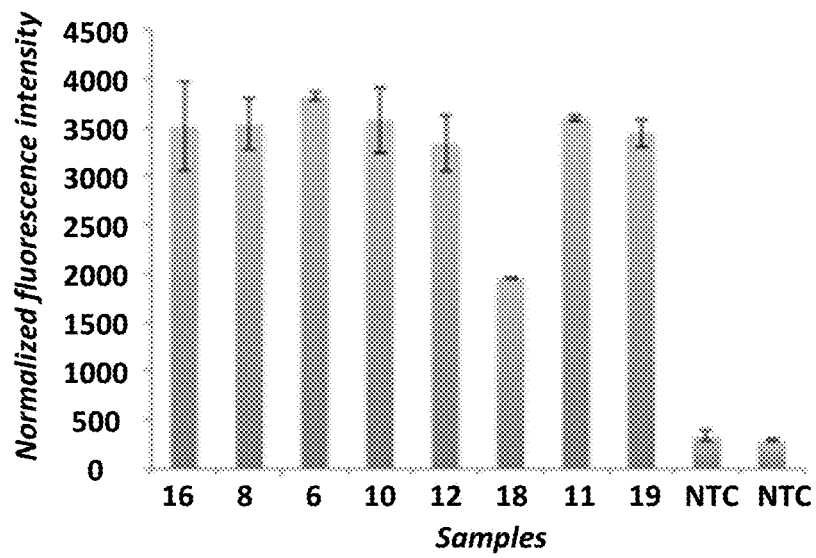
FIG. 10A-10B shows detection of the human anti-p24 antibody in HIV-positive samples. Assays were conducted with beads using HIV p24 as the capture protein and anti-human IgG antibody as the detection antibody. Provided are data for HIV-positive samples (labeled numerically) and negative control (labeled "NTC," "NTC1," or "NTC2").
Figure 10B:
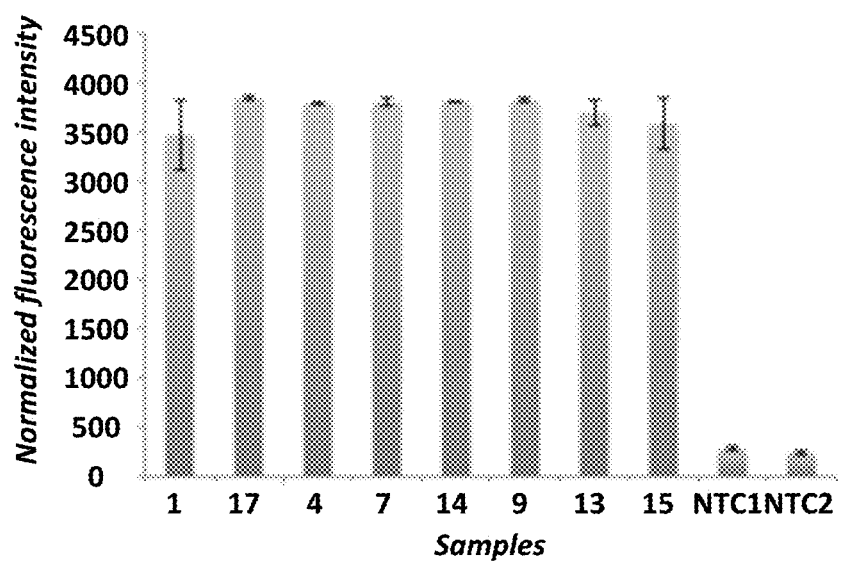

Various HIV-related proteins could be detected in HIV-positive samples. One study included detection of HIV p24 protein in HIV-positive samples (FIG. 9A-9B) or the detection of human anti-p24 antibody (FIG. 10A-10B). As seen in FIG. 9A-9B, among the 19 available HIV-positive samples, one of the samples had lysed red blood cells and could not be analyzed. The remaining 18 HIV-positive samples were treated with HCl—NaOH/HEPES buffer and analyzed for presence of antibodies and proteins. The assays for protein detection could not detect p24 protein in two of the samples (samples 11 and 18). Without wishing to be limited by mechanism, various possible explanations exist. In one non-limiting instance, the HIV infection could be established (e.g., older than 3-5 months), such that the antibodies have higher avidity and do not release the protein even after the buffer treatment. In another non-limiting instance, the patients could be undergoing an HIV treatment and may no longer have a detectable amount of the virus. On the other hand, detection of human anti-p24 antibody did not show any false-negatives for any of the samples (FIG. 10A-10B). The negative control for both protein assays (FIG. 9A-9B) and antibody assays (FIG. 10A-10B) were the HIV-negative samples.

Figure 11:
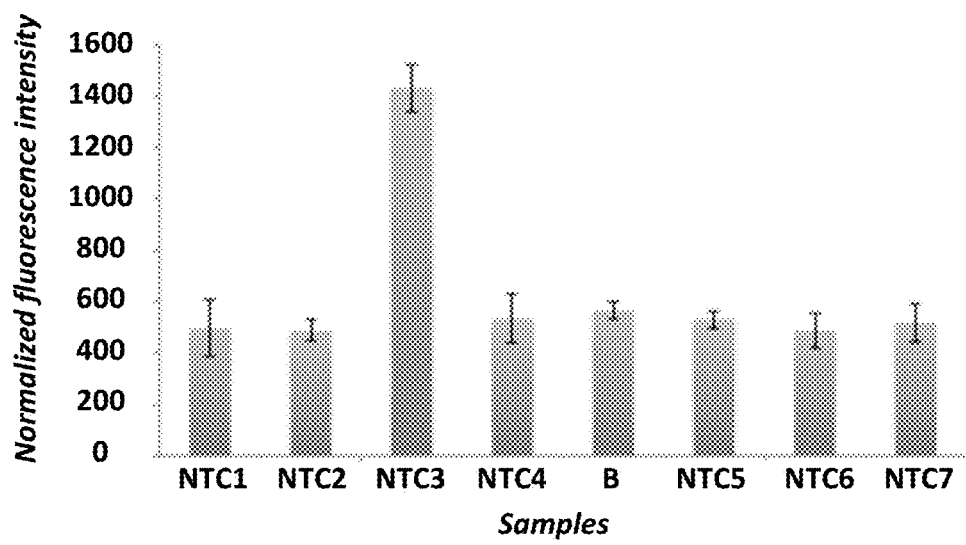
FIG. 11 shows detection of human anti-p24 antibody in HIV-negative samples. Assays were conducted with beads using HIV p24 as the capture protein and anti-human IgG antibody as the detection antibody. Provided are data for HIV-negative samples (labeled "NTC1" to "NTC7") and buffer (labeled "B").

Negative control experiments were conducted (FIG. 11). An assay was performed on HIV-negative samples that were previously determined by PCR. Among seven samples, one was a false-positive (sample NTC3 in FIG. 11). The negative control for the NTC samples were the assays performed in buffer. The detection of human anti-p24 antibodies in negative control samples gave negative results. There were no false-positives. The negative control for NTC samples were wash buffer samples for both protein and antibody detection assays. The capture beads for antibody assay detection had p24 protein beads and the detection antibody was anti-human antibody.

CONCLUSIONS

One goal of this work was to develop a multiplexed assay for detection of proteins that are secreted by *M. tuberculosis* in HIV-positive patients. The detection of secreted proteins is one reliable diagnostic method to confirm the presence of an acute ongoing disease, as opposed to detection of host-responsive antibodies that can be present also during latent infection. As shown, the bead-based immunoassay described herein is rapid (e.g., 30 minutes from a sample-to-answer time), simple, and sensitive (e.g., detection of secreted proteins at very low pg/mL levels in human serum samples). In a multiplexed assay, the limit of detection was as follows: 6.93 pg/mL for the HIV p24 protein, 5.62e6 ab/mL for the human anti-p24 antibody, 7.53 pg/mL for the TB Ag85B protein, and 53.32 pg/mL for the TB 38-kDa protein. Furthermore, the assay can be used for detection of other proteins of interest by substituting the capture and detection antibodies. Adapting the assay for the desired target of interest can be achieved within a short period of time.

To confirm the spiked assays, clinical samples with known infection status were analyzed for various HIV-related and TB-related proteins. Two available TB samples were confirmed to have the secreted TB proteins and human antibodies by our assay. Among the 18 HIV-positive samples, only 16 samples were confirmed to have the p24 protein present (two were false-negative), and all 18 samples were confirmed to have the human anti-p24 antibodies. Among the seven available HIV-negative samples, one sample provided a false positive result for HIV p24 protein detection. None of the negative samples were positive for human anti-p24 antibody detection. During the cross-reactivity check, one of the TB detection antibodies was found to cross-react with one of the HIV antibodies, giving an elevated background, but not a dose response curve. Overall, the HIV assay displayed a sensitivity of 89% and a specificity of 85%.

The results herein provide proof-of-concept data that shows detection of an active tuberculosis disease based on capture and detection of bacterial secreted proteins from serum samples. All proteins and antibody dilutions corresponded to dose-response curves. The proteins and the human immune response antibodies were detected with a definite "yes" or "no" answer. The platform can be adapted for single protein detection or multiplexed detection, making this assay potentially useful in the clinical diagnosis of both HIV and tuberculosis infectious states.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method comprising:
   providing a mixture comprising a sample, the sample comprising an anti-Ag85 antibody or an anti-p24 antibody that binds to a first target of interest, the sample treated with a dissociation agent, wherein the dissociation agent comprises an acid or an acidic buffer and wherein the dissociation agent is configured to dissociate the anti-Ag85 antibody or the anti-p24 antibody from the first target of interest;
   neutralizing the mixture with a neutralization agent configured to neutralize the dissociation agent, thereby providing a treated mixture comprising a neutralized, dissociated sample, wherein the neutralization agent comprises a base or a basic buffer;
   layering the treated mixture on a density medium disposed within a detection chamber that is disposed within a substrate, wherein the treated mixture further comprises a first population of beads characterized by a first density and/or a first radius, and wherein the first population of beads is configured to bind to the first target of interest;
   subjecting the treated mixture to a sedimentation force such that the first population of beads, or a portion thereof, travels through the density medium, wherein the density medium is characterized by a density that is less than the first density of the first population of beads; and detecting a presence or absence of a signal from one or more detection agents bound directly or indirectly to the first population of beads, or a portion thereof.

2. The method of claim 1, wherein the sample comprises a non-host protein that binds to the first target of interest, and wherein the dissociation agent is configured to dissociate the non-host protein from the first target of interest.

3. The method of claim 1, wherein the sample comprises a plurality of targets of interest and a plurality of host-responsive proteins that bind to the plurality of targets of interest and/or a plurality of non-host proteins that bind to the plurality of targets of interest.

4. The method of claim 1, wherein the sample comprises the first target of interest indicative of a bacterial infection and a second target of interest indicative of a viral infection.

5. The method of claim 1, wherein the first target of interest is a host-derived protein, a non-host derived protein, an antibody, an antigen, a peptide, a nucleic acid, a protein modified by a non-host pathogen, a nucleic acid modified by a non-host pathogen, or a cell modified by a non-host pathogen.

6. The method of claim 1, wherein a portion of the treated mixture comprises one or more components that is characterized by a density that is less than the density of the density medium.

7. The method of claim 1, wherein said neutralizing further comprises providing the treated mixture within a channel or a chamber disposed within the substrate.

8. The method of claim 1, wherein said layering further comprises transporting the treated mixture to the detection chamber by way of a channel disposed within the substrate, and wherein said transporting comprises spinning the substrate.

9. The method of claim 1, wherein said subjecting comprises spinning the substrate.

10. The method of claim 1, wherein the first population of beads is configured to bind to a second target of interest that is different from the first target of interest.

11. The method of claim 1, wherein the treated mixture further comprises a second population of beads characterized by a second density that is different than the first density, and wherein the second population of beads is configured to bind to a second target of interest that is different from the first target of interest; or wherein the treated mixture further comprises a second population of beads characterized by a second radius that is different than the first radius, and wherein the second population of beads is configured to bind to a second target of interest that is different from the first target of interest.

12. The method of claim 1, wherein the treated mixture further comprises one or more detection agents configured to bind directly or indirectly to the first population of beads, or a portion thereof, if in the presence of the target of interest.

13. The method of claim 12, wherein the first population of beads further comprises one or more capture agents configured to bind the first target of interest, thereby forming a population of captured target-bead complexes; and wherein the one or more detection agents is configured to bind to the population of captured target-bead complexes, or a portion thereof.

14. The method of claim 2, wherein the non-host protein is an Ag85A protein, an Ag85B protein, an Ag85C protein, a tuberculosis 38-kDa protein, or a HIV p24 protein.

15. A method comprising:
providing a mixture comprising a sample treated with a dissociation agent, wherein the dissociation agent comprises an acid or an acidic buffer, and wherein the mixture comprises a first target of interest and a second target of interest;

neutralizing the mixture with a neutralization agent configured to neutralize the dissociation agent, thereby providing a treated mixture comprising a neutralized, dissociated sample, wherein the neutralization agent comprises a base or a basic buffer;

layering the treated mixture on a density medium disposed within a detection chamber that is disposed within a substrate, wherein the treated mixture further comprises a first population of beads characterized by a first density and/or a first radius and a second population of beads characterized by a second density and/or a second radius, wherein the first population of beads is configured to bind to the first target of interest, and wherein the second population of beads is configured to bind the second target of interest;

subjecting the treated mixture to a sedimentation force such that the first population of beads and the second population of beads, or a portion thereof, travels through the density medium, wherein the density medium is characterized by a density that is less than the first density of the first population of beads and that is less than the second density of the second population of beads; and detecting a presence or absence of a signal from one or more detection agents bound directly or indirectly to the first population of beads and to the second population of beads, or a portion thereof.

16. The method of claim 15, wherein the first target of interest is indicative of a bacterial infection and wherein the second target of interest is indicative of a viral infection.

17. The method of claim 15, wherein the sample comprises a host-responsive protein that binds to the first target of interest, and wherein the host-responsive protein is an anti-Ag85 antibody or an anti-p24 antibody.

18. The method of claim 15, wherein the sample comprises a non-host protein that binds to the second target of interest, and wherein the non-host protein is an Ag85A protein, an Ag85B protein, an Ag85C protein, a tuberculosis 38-kDa protein, or a HIV p24 protein.

19. A method comprising:
providing a mixture comprising a sample, the sample comprising an Ag85A protein, an Ag85B protein, an Ag85C protein, a tuberculosis 38-kDa protein, or a HIV p24 protein that binds to a first target of interest, the sample treated with a dissociation agent, wherein the dissociation agent comprises an acid or an acidic buffer and wherein the dissociation agent is configured to dissociate the Ag85A protein, the Ag85B protein, the Ag85C protein, the tuberculosis 38-kDa protein, or the HIV p24 protein from the first target of interest;

neutralizing the mixture with a neutralization agent configured to neutralize the dissociation agent, thereby providing a treated mixture comprising a neutralized, dissociated sample, wherein the neutralization agent comprises a base or a basic buffer;

layering the treated mixture on a density medium disposed within a detection chamber that is disposed within a substrate, wherein the treated mixture further comprises a first population of beads characterized by a first density and/or a first radius, and wherein the first population of beads is configured to bind to the first target of interest;

subjecting the treated mixture to a sedimentation force such that the first population of beads, or a portion thereof, travels through the density medium, wherein the density medium is characterized by a density that is less than the first density of the first population of beads; and detecting a presence or absence of a signal from one or more detection agents bound directly or indirectly to the first population of beads, or a portion thereof.

* * * * *